(12) United States Patent
Zemlok et al.

(10) Patent No.: US 7,887,530 B2
(45) Date of Patent: Feb. 15, 2011

(54) POWERED SURGICAL INSTRUMENT

(75) Inventors: Michael A. Zemlok, Prospect, CT (US); David C. Racenet, Litchfield, CT (US); Adam J. Ross, East Hampton, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 360 days.

(21) Appl. No.: 12/012,108

(22) Filed: Jan. 31, 2008

(65) Prior Publication Data
US 2008/0255418 A1 Oct. 16, 2008

Related U.S. Application Data

(63) Continuation of application No. 11/786,934, filed on Apr. 13, 2007.

(51) Int. Cl.
*A61B 17/03* (2006.01)
(52) U.S. Cl. .......................... 606/1; 600/118
(58) Field of Classification Search ............... 606/1, 606/25
See application file for complete search history.

(56) References Cited

U.S. PATENT DOCUMENTS

| | | | |
|---|---|---|---|
| 2,593,882 A * | 4/1952 | Hercik ........................ 74/44 |
| 3,653,282 A * | 4/1972 | Bouffiou et al. ............ 74/815 |
| 4,331,277 A | 5/1982 | Green |
| 4,362,977 A * | 12/1982 | Evans et al. ............ 700/254 |
| 4,606,343 A | 8/1986 | Conta et al. |
| 5,312,023 A | 5/1994 | Green et al. |
| 5,326,013 A | 7/1994 | Green et al. |
| 5,350,355 A | 9/1994 | Sklar |
| 5,389,098 A | 2/1995 | Tsuruta et al. |
| 5,467,911 A | 11/1995 | Tsuruta et al. |
| 5,518,163 A | 5/1996 | Hooven |
| 5,518,164 A | 5/1996 | Hooven |
| 5,526,822 A | 6/1996 | Burbank et al. |
| 5,649,956 A * | 7/1997 | Jensen et al. ............. 606/205 |
| 5,653,374 A | 8/1997 | Young et al. |
| 5,667,517 A * | 9/1997 | Hooven ..................... 606/151 |
| 5,779,130 A | 7/1998 | Alesi et al. |

(Continued)

FOREIGN PATENT DOCUMENTS

WO  WO03/026511  4/2003

OTHER PUBLICATIONS

European Search Report for corresponding EP 08252703date of mailing is Oct. 31, 2008 (3 pages).

(Continued)

*Primary Examiner*—Henry M Johnson, III
*Assistant Examiner*—Jeffrey B Lipitz

(57) ABSTRACT

A surgical instrument including a housing, an endoscopic portion, a drive gear, a drive motor, a shift motor and an end effector is disclosed. The endoscopic portion extends distally from the housing and defines a longitudinal axis. The drive gear is disposed at least partially within the housing and is rotatable about a drive gear axis which extends therethrough. The drive gear is selectively movable along the drive gear axis. The drive motor is disposed in mechanical cooperation with the drive gear and is configured to rotate the drive gear. The shift motor is disposed in mechanical cooperation with the drive gear and is configured to move the drive gear along the drive gear axis. The end effector is disposed adjacent a distal portion of the endoscopic portion.

28 Claims, 16 Drawing Sheets

U.S. PATENT DOCUMENTS

| | | |
|---|---|---|
| 5,782,397 A | 7/1998 | Koukline |
| 5,954,259 A | 9/1999 | Viola et al. |
| 6,461,372 B1 | 10/2002 | Jensen et al. |
| 6,533,157 B1 | 3/2003 | Whitman |
| 6,699,177 B1 | 3/2004 | Wang et al. |
| 6,716,233 B1 | 4/2004 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,981,941 B2 | 1/2006 | Whitman et al. |
| 2001/0007944 A1* | 7/2001 | Mark et al. .................. 606/170 |
| 2002/0087179 A1* | 7/2002 | Culp et al. .................. 606/167 |
| 2003/0066284 A1* | 4/2003 | Chakkera et al. ........... 60/226.2 |
| 2005/0192609 A1 | 9/2005 | Whitman et al. |
| 2005/0220639 A1* | 10/2005 | Sasaki et al. ................. 417/415 |
| 2007/0175961 A1 | 8/2007 | Shelton et al. |

OTHER PUBLICATIONS

European Search Report for corresponding EP 08251357 date of mailing is Sep. 29, 2009 (3 pages).

* cited by examiner

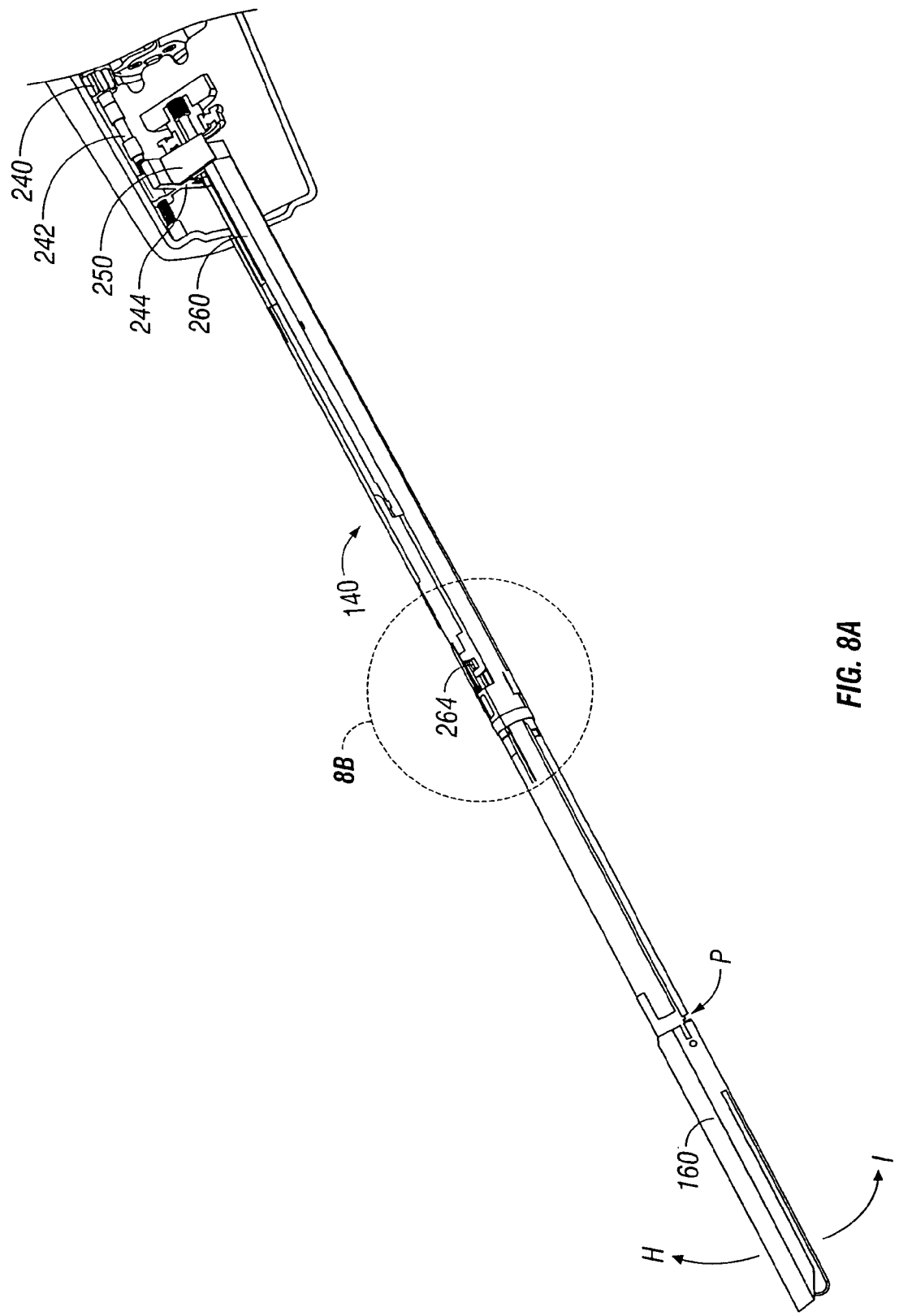

POWERED SURGICAL INSTRUMENT

CROSS REFERENCE TO RELATED APPLICATIONS

This application is a continuation of U.S. patent application Ser. No. 11/786,934 filed Apr. 13, 2007, the disclosure of which is hereby incorporated by reference herein, in their entirety.

BACKGROUND

1. Technical Field

The present disclosure relates to surgical instruments for fastening body tissue and, more particularly, to a powered surgical instrument having a drive gear configured to be movable to affect rotation, articulation and actuation of the instrument.

2. Background Of Related Art

Surgical devices wherein tissue is first grasped or clamped between opposing jaw structure and then joined by surgical fasteners are well known in the art. In some instruments, a knife is provided to cut the tissue which has been joined by the fasteners. The fasteners typically include surgical staples and two part polymeric fasteners.

Instruments for this purpose may include two elongated members which are respectively used to capture or clamp tissue. Typically, one of the members carries a staple cartridge that houses a plurality of staples arranged in rows while the other member has an anvil that defines a surface for forming the staple legs as the staples are driven from the staple cartridge. Several instruments include clamps, handles and/or knobs to affect actuation along with rotation and articulation of an end effector. Such surgical instruments can require the user to exert a significant force in operating the handles, knobs, etc., and require more than one hand to operate the instrument.

Surgical instruments with actuators that require less force to operate are desired. In addition, surgical instruments which perform multiple functions with one-handed operation are also desired.

SUMMARY

The present disclosure relates to a surgical instrument including a housing, an endoscopic portion, a drive gear, a drive motor, a shift motor and an end effector. The endoscopic portion extends distally from the housing and defines a longitudinal axis. The drive gear is disposed at least partially within the housing and is rotatable about a drive gear axis which extends therethrough. The drive gear is selectively movable along the drive gear axis. The drive motor is disposed in mechanical cooperation with the drive gear and is configured to rotate the drive gear. The shift motor is disposed in mechanical cooperation with the drive gear and is configured to move the drive gear along the drive gear axis. The end effector is disposed adjacent a distal portion of the endoscopic portion.

The surgical instrument further includes, in certain embodiments, a ring gear disposed at least partially within the housing, the drive gear being movable to a position along the drive gear axis to matingly engage the ring gear. Rotation of the ring gear rotates the end effector about the longitudinal axis. The instrument may include an actuator gear disposed at least partially within the housing, the drive gear being movable to a position along the drive gear axis to matingly engage the actuator gear. Rotation of the actuator gear causes at least a partial actuation of the end effector.

The end effector defines a second longitudinal axis and the end effector is desirably movable from a first position where the second longitudinal axis is substantially aligned with the first longitudinal axis to at least a second position where the second longitudinal axis is disposed at an angle to the first longitudinal axis. The surgical instrument may include an articulation gear disposed at least partially within the housing, the drive gear being movable to a position along the drive gear axis to matingly engage the articulation gear. Rotation of the articulation gear causes the end effector to move from its first position towards its second position. In certain embodiments, the drive gear is selectively movable along the drive gear axis between three distinct positions.

In certain embodiments, the surgical instrument further comprises a user interface, the user interface including a screen that displays readable information. The user interface may include at least one switch that controls the position of the drive gear along the drive gear axis. The user interface can include at least one switch that controls the rotation speed of the drive gear.

The housing may further include a distal housing portion and a proximal housing portion, the distal housing portion being rotatable about the longitudinal axis relative to the proximal housing portion. The distal housing portion and proximal housing portion may define one or more detents. In one embodiment, the distal housing portion has a plurality of detents thereon and the proximal housing portion includes a tab thereon. The tab is distally biased and in mechanical cooperation with a detent disposed on the distal housing portion.

The housing desirably includes a handle portion disposed along a handle axis. In certain embodiments, the handle axis is substantially parallel to the drive gear axis.

The present disclosure also relates to a method of applying surgical fasteners to tissue. The method of this embodiment includes providing a powered surgical instrument which includes a housing, an endoscopic portion, a drive gear and an end effector. The endoscopic portion extends distally from the housing and defines a longitudinal axis. The drive gear is disposed at least partially within the housing and is rotatable about a drive gear axis extending therethrough. The drive gear is selectively movable along the drive gear axis. The end effector is disposed adjacent a distal portion of the endoscopic portion. The method further includes moving the drive gear along the drive gear axis and rotating the drive gear about the drive gear axis.

In certain embodiments, the end effector is rotated about the longitudinal axis. The end effector may define a second longitudinal axis and the end effector may be movable from a first position where the second longitudinal axis is substantially aligned with the first longitudinal axis to at least a second position where the second longitudinal axis is disposed at an angle to the first longitudinal axis. In certain embodiments, the end effector is moved from its first position towards its second position.

In certain embodiments, the drive gear is selectively movable along the drive gear axis between three distinct positions. Two of the three positions desirably correspond to rotating the end effector and actuating the powered surgical instrument.

In a further aspect, a surgical stapling instrument, comprises: a housing; an endoscopic portion extending distally from the housing and defining a longitudinal axis; an end effector adjacent a distal end of the endoscopic portion and being pivotably mounted for articulation with respect to the endoscopic portion; a drive assembly for deploying surgical staples from the end effector into tissue; a drive motor having a drive member, the drive member being movable from a first position to at least a second position; an articulation member arranged for engagement by the drive member in the first position, the articulation member being connected to the end effector so that movement of the articulation member by the drive member articulates the end effector with respect to the endoscopic portion; and an actuation member arranged for engagement by the drive member in the second position, the actuation member being connected to the drive assembly so that movement of the actuation member by the drive member deploys the surgical staples.

The surgical stapling instrument may include a rotation member connected to the endoscopic portion and arranged for engagement by the drive member so that movement of the drive member rotates the endoscopic portion around the longitudinal axis. The end effector has a cartridge assembly, surgical staples disposed in the cartridge assembly, and an anvil assembly disposed adjacent the cartridge assembly, in certain preferred embodiments. The cartridge assembly and anvil assembly are movable from an open position to an approximated position with respect to one another for engaging tissue between the cartridge assembly and anvil assembly. The movement of the actuation member may approximate the cartridge assembly and anvil assembly with respect to one another before deploying the surgical staples.

In another aspect, a surgical stapling instrument, comprises: a housing; an endoscopic portion extending distally from the housing and defining a longitudinal axis; an end effector disposed adjacent a distal end of the endoscopic portion; a drive assembly for deploying surgical staples from the end effector into tissue; a drive motor having a drive member, the drive member being movable from a first position to at least a second position; a rotation member arranged for engagement by the drive member in the first position, the rotation member being connected to the endoscopic portion so that movement of the rotation member by the drive member rotates the endoscopic portion; and an actuation member arranged for engagement by the drive member in the second position, the actuation member being connected to the drive assembly so that movement of the actuation member by the drive member deploys the surgical staples.

The surgical stapling instrument may include an articulation member arranged for engagement by the drive member, the articulation member being connected to the end effector so that movement of the articulation member by the drive member articulates the end effector with respect to the endoscopic portion. In certain embodiments, the end effector has a cartridge assembly, surgical staples disposed in the cartridge assembly, and an anvil assembly disposed adjacent the cartridge assembly. The cartridge assembly and anvil assembly are movable from an open position to an approximated position with respect to one another for engaging tissue between the cartridge assembly and anvil assembly. The movement of the actuation member may approximate the cartridge assembly and anvil assembly with respect to one another before deploying the surgical staples.

In a further aspect, a surgical stapling instrument, comprises: a housing; an endoscopic portion extending distally from the housing; a drive motor disposed at least partially within the housing and having a drive member; an end effector connected adjacent a distal end of the endoscopic portion for articulation with respect to the endoscopic portion, the end effector being connected to an articulation member driven by the drive motor, the end effector having surgical staples arranged to be deployed in tissue; and a power source disposed at least partially within the housing and arranged to provide power to the drive motor.

In certain preferred embodiments, the end effector forms the distal end of a loading unit, the loading unit having a proximal body portion configured for connection to the endoscopic portion. For example, the endoscopic portion has a distal end configured for connection with a first type of loading unit and at least a second type of loading unit having a second surgical function, the first type being an articulating surgical stapling loading unit and the second type being a non-articulating surgical stapling loading unit.

In another aspect, a surgical instrument comprises: a housing; an endoscopic portion extending distally from the housing and defining a longitudinal axis; an end effector at a distal end of the endoscopic portion and arranged for articulation with respect to the endoscopic portion; a drive shaft arranged for translation along the longitudinal axis and for engaging the end effector; a motor assembly arranged to selectively drive one or more functions of the end effector; and a display component for displaying a condition of the end effector.

The display component may be an operating room monitor. The function of the end effector may be selected from the group consisting of: rotation of the endoscopic portion about the longitudinal axis, movement of the drive shaft along the longitudinal axis, and articulation of the end effector.

The surgical instrument desirably includes a digital control module in the housing. The digital control module transmits information concerning the operation of the end effector to the display component. The display component may be disposed at least partially in the housing.

In another aspect, a surgical instrument, comprises: a housing; an endoscopic portion extending distally from the housing and defining a longitudinal axis; a drive tube rotatable about a drive tube axis extending therethrough; a drive motor disposed at least partially within the housing, the drive motor being movable into engagement with the drive tube; a rod disposed in mechanical cooperation with the drive tube, at least a portion of the rod being translatable with respect to the drive tube; and an end effector disposed adjacent a distal portion of the endoscopic portion, the end effector being arranged to be actuated by rod so that the firing rod drives a surgical function of the end effector.

In certain embodiments, a clutch disposed between the drive motor and the drive tube, the clutch including a clutch plate and a spring. The clutch plate may be arranged to mate with an interface at a proximal end of the drive tube.

In certain preferred embodiments, the end effector defines a second longitudinal axis, the end effector being movable from a first position where the second longitudinal axis is substantially aligned with the first longitudinal axis to at least a second position where the second longitudinal axis is disposed at an angle to the first longitudinal axis. The end effector is desirably rotatable about the first longitudinal axis with respect to the housing.

In certain preferred embodiments, a user interface including at least one switch that controls the translation of the rod is included. At least a portion of the rod is desirably disposed at least partially within the drive tube. In certain embodiments, the drive tube includes a threaded portion on an interior surface thereof. The rod includes a threaded portion thereon, the threaded portion of the firing rod being engagable with the threaded portion of the drive tube. At least a portion of the rod may be arranged to extend through an aperture of a plate, the aperture including a non-round cross-section for preventing rotation of the firing rod with respect to the plate.

In certain embodiments, a power source is disposed at least partially within the housing and arranged to provide power to the drive motor. The end effector may be part of a disposable loading unit.

DESCRIPTION OF THE DRAWINGS

An embodiment of the presently disclosed powered surgical instrument is disclosed herein with reference to the drawings, wherein:

FIG. 8A is a partial perspective view including an endoscopic portion of the powered surgical instrument of FIGS. 1-7 according to an embodiment of the present disclosure;

DETAILED DESCRIPTION OF EMBODIMENTS

Figure 1:
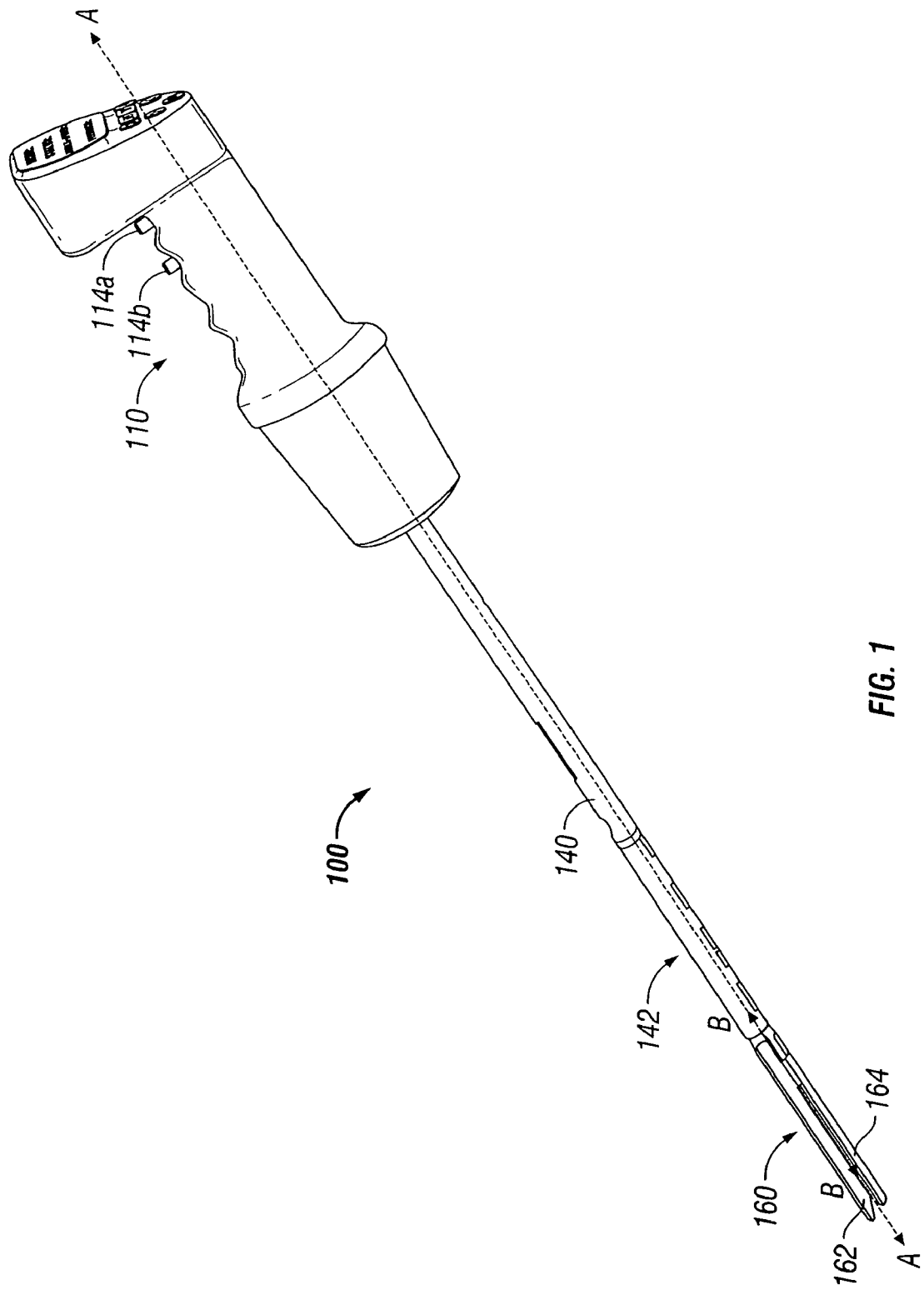
FIG. 1 is a perspective view of a powered surgical instrument according to an embodiment of the present disclosure.

Embodiments of the presently disclosed powered surgical instrument are now described in detail with reference to the drawings, in which like reference numerals designate identical or corresponding elements in each of the several views. As used herein the term "distal" refers to that portion of the powered surgical instrument, or component thereof, farther from the user while the term "proximal" refers to that portion of the powered surgical instrument or component thereof, closer to the user.

A powered surgical instrument, e.g., a surgical stapler, in accordance with the present disclosure is referred to in the figures as reference numeral 100. Referring initially to FIG. 1, powered surgical instrument 100 includes a housing 110, an endoscopic portion 140 defining a longitudinal axis A-A extending therethrough, and an end effector 160, defining a longitudinal axis B-B (illustrated substantially aligned with axis A-A in FIG. 1) extending therethrough. Endoscopic portion 140 extends distally from housing 110 and end effector 160 is disposed adjacent a distal portion 142 of endoscopic portion 140.

Figure 2:
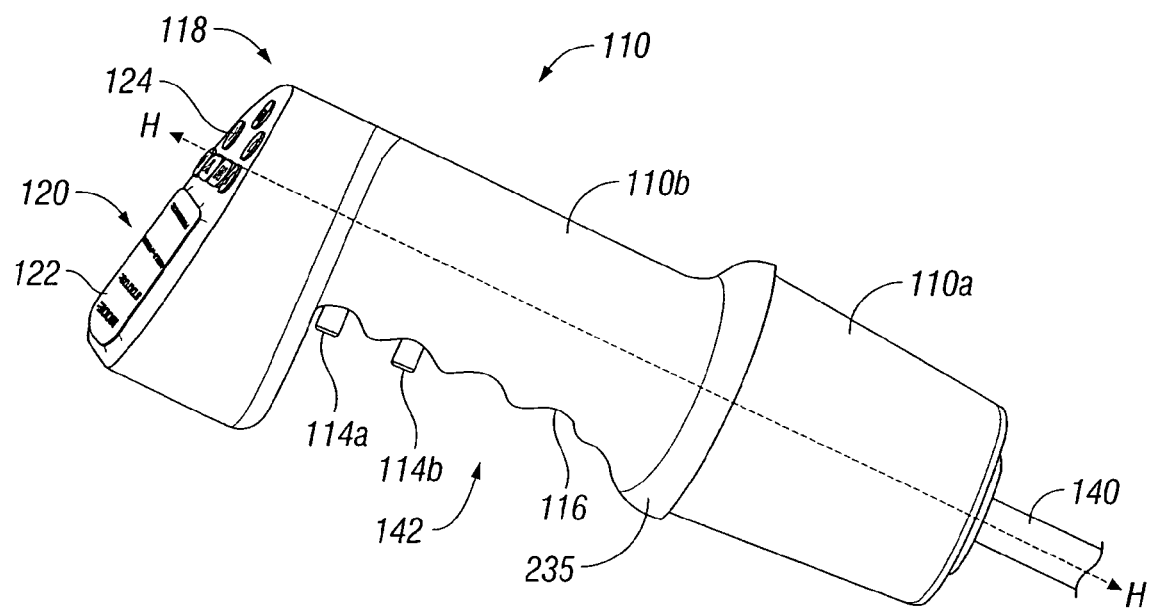
FIG. 2 is an enlarged partial perspective view of the powered surgical instrument of FIG. 1.
Figure 3:
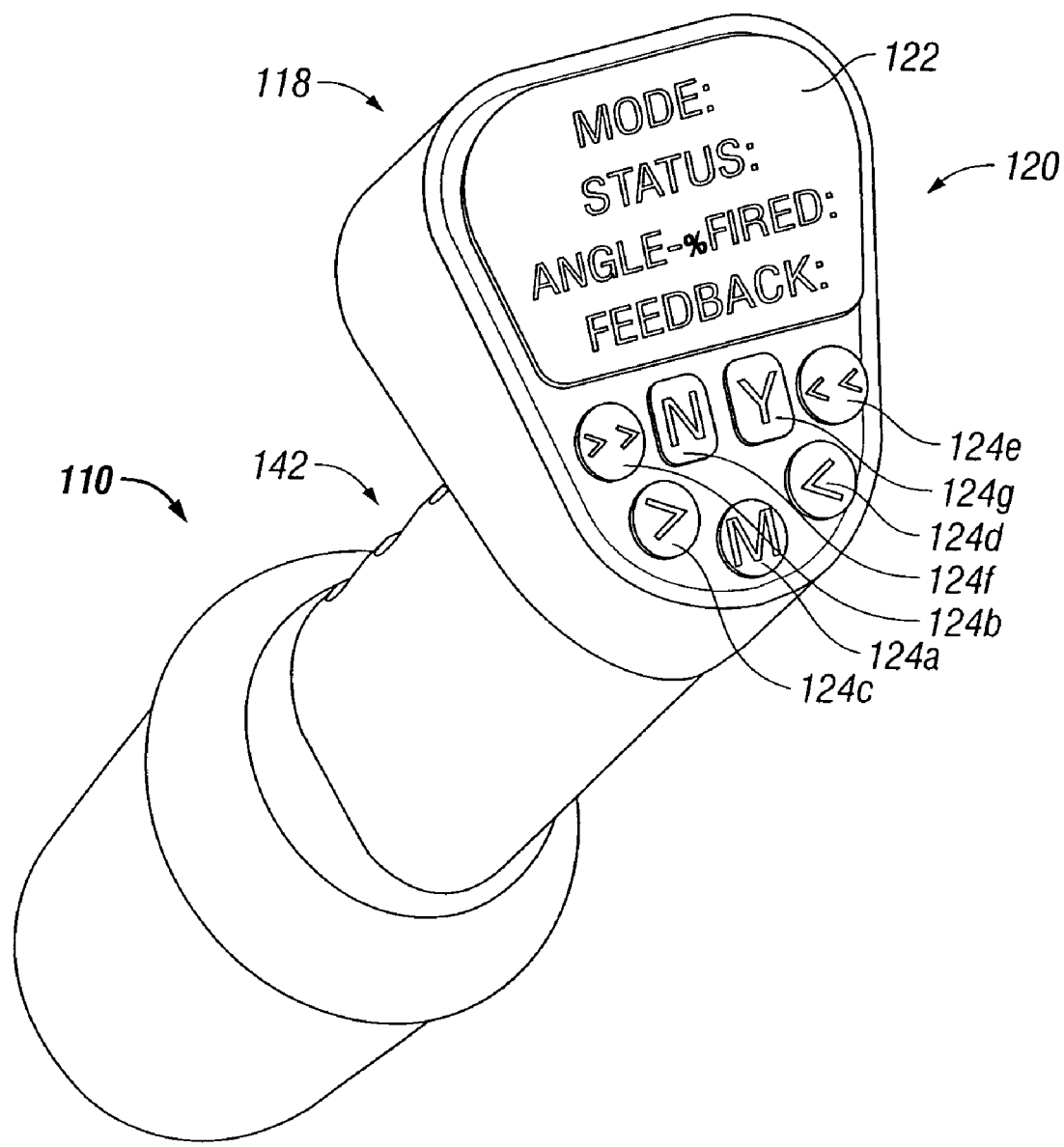
FIG. 3 is an enlarged partial perspective view of the powered surgical instrument of FIGS. 1 and 2.

With reference to FIGS. 2 and 3, an enlarged view of housing 110 is illustrated according to an embodiment of the present disclosure. In the illustrated embodiment, housing 110 includes a handle portion 112 having at least one button 114 thereon (two buttons 114a and 114b are shown). Handle portion 112, which defines a handle axis H-H, is shown having indentations 116 that correspond to fingers of a user. Each button 114a and 114b is shown as being disposed on an indentation 116 to facilitate its depression by a user's finger.

With continued reference to FIGS. 2 and 3, a proximal area 118 of housing 110 includes a user interface 120. In the illustrated embodiment, user interface 120 includes a screen 122 and at least one switch 124 (seven switches 124a-124g are shown). Screen 122 displays readable information thereon, including status information of powered surgical instrument 100 in an embodiment. Switches 124a-124g control various actions of powered surgical instrument 100, as is described in detail below.

FIGS. 4-7, 9-11 and 14 illustrate various internal components of powered surgical instrument 100, including a drive gear 200 or drive member, a drive motor 210 and a shift motor 220. It is envisioned that a three-position solenoid, for instance, can be used as an alternative to shift motor 220. Drive gear 200 is rotatable about a drive gear axis C-C extending therethrough (FIG. 4) and is selectively movable along drive gear axis C-C. Drive motor 210 is disposed in mechanical cooperation with drive gear 200 and is configured to rotate drive gear 200 about drive gear axis C-C. Shift motor 220 is disposed in mechanical cooperation with drive gear 200 (drive motor 210 is illustrated between drive gear 200 and shift motor 220 in accordance with a disclosed embodiment) and is configured to translate drive gear 200 axially along drive gear axis C-C. In a disclosed embodiment, drive motor 210 and/or shift motor 220 may be a motor or a gear motor, which may include gearing incorporated within its housing.

Shift motor 220 is configured to selectively move drive gear 200 between a plurality of positions; three positions are shown in the illustrated embodiments. The first position, illustrated in FIGS. 5 and 6, enables rotation of end effector 160; the second position, illustrated in FIG. 7, enables articulation of end effector 160; and the third position, illustrated in FIGS. 9-11 and 14, enables actuation of powered surgical instrument 100.

Figure 5:
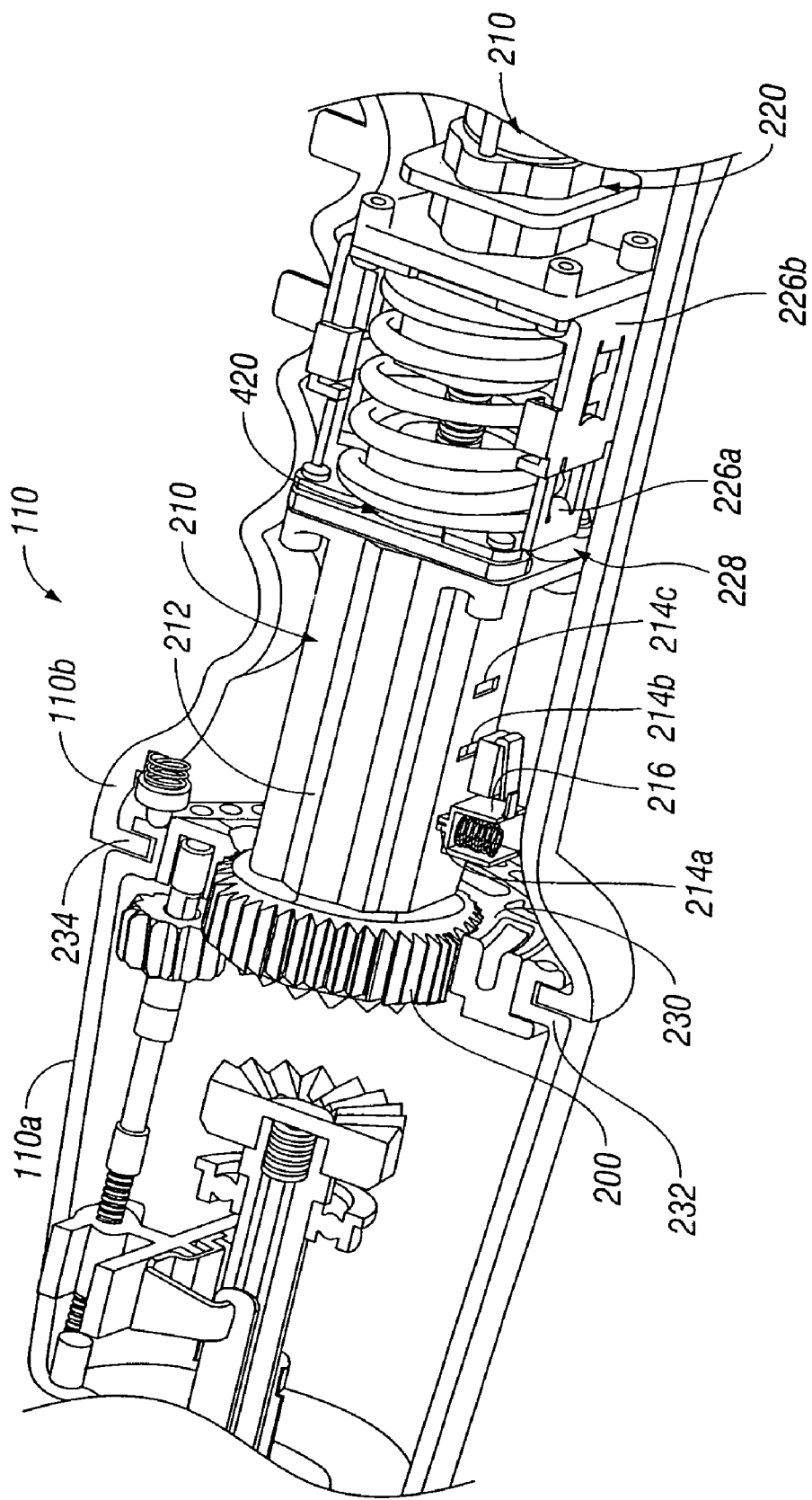
FIGS. 5 and 6 are partial perspective sectional views showing the internal components of the powered surgical instrument of FIGS. 1-4 disposed in a first position.
Figure 6:
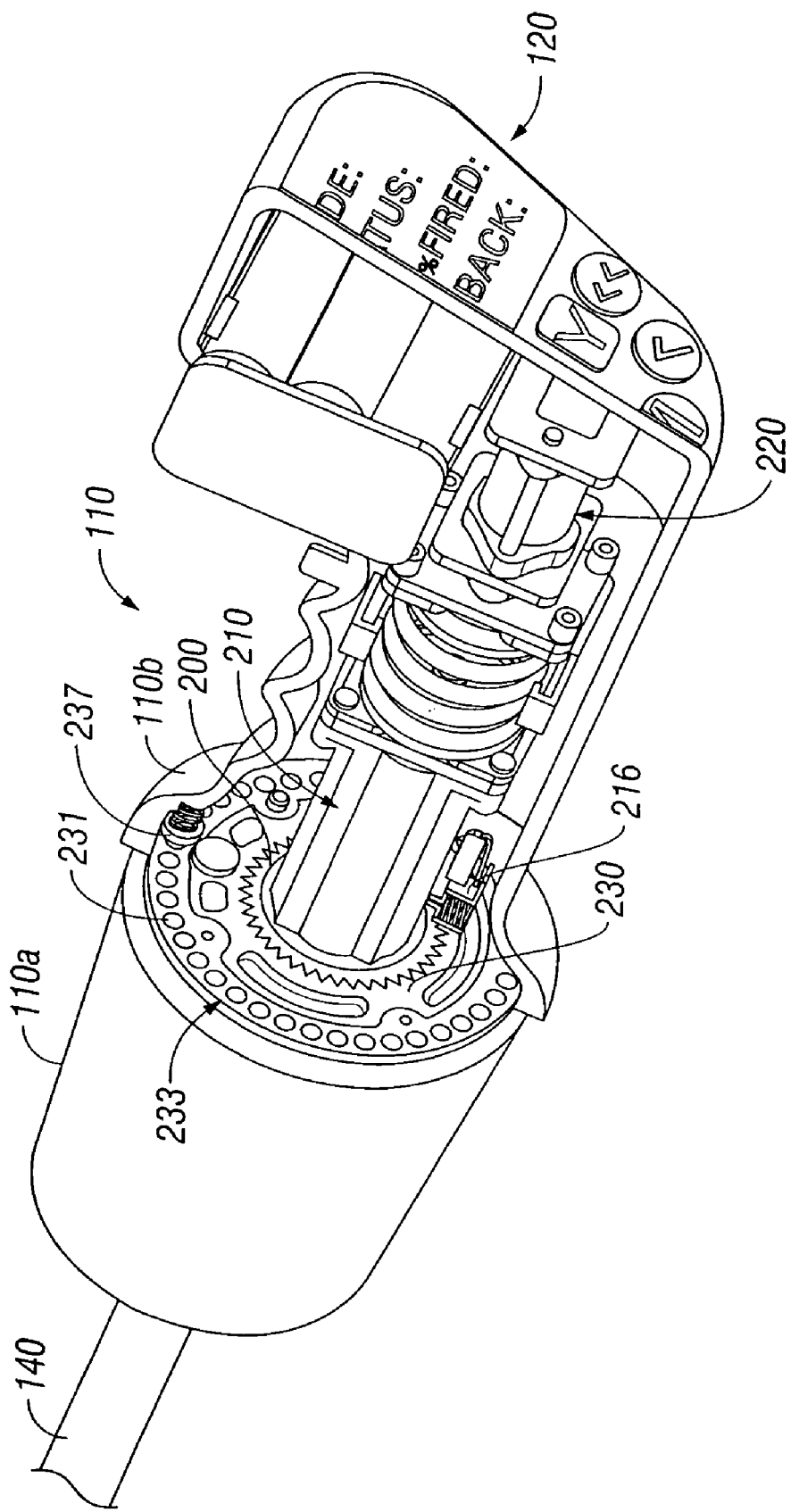
Figure 7:
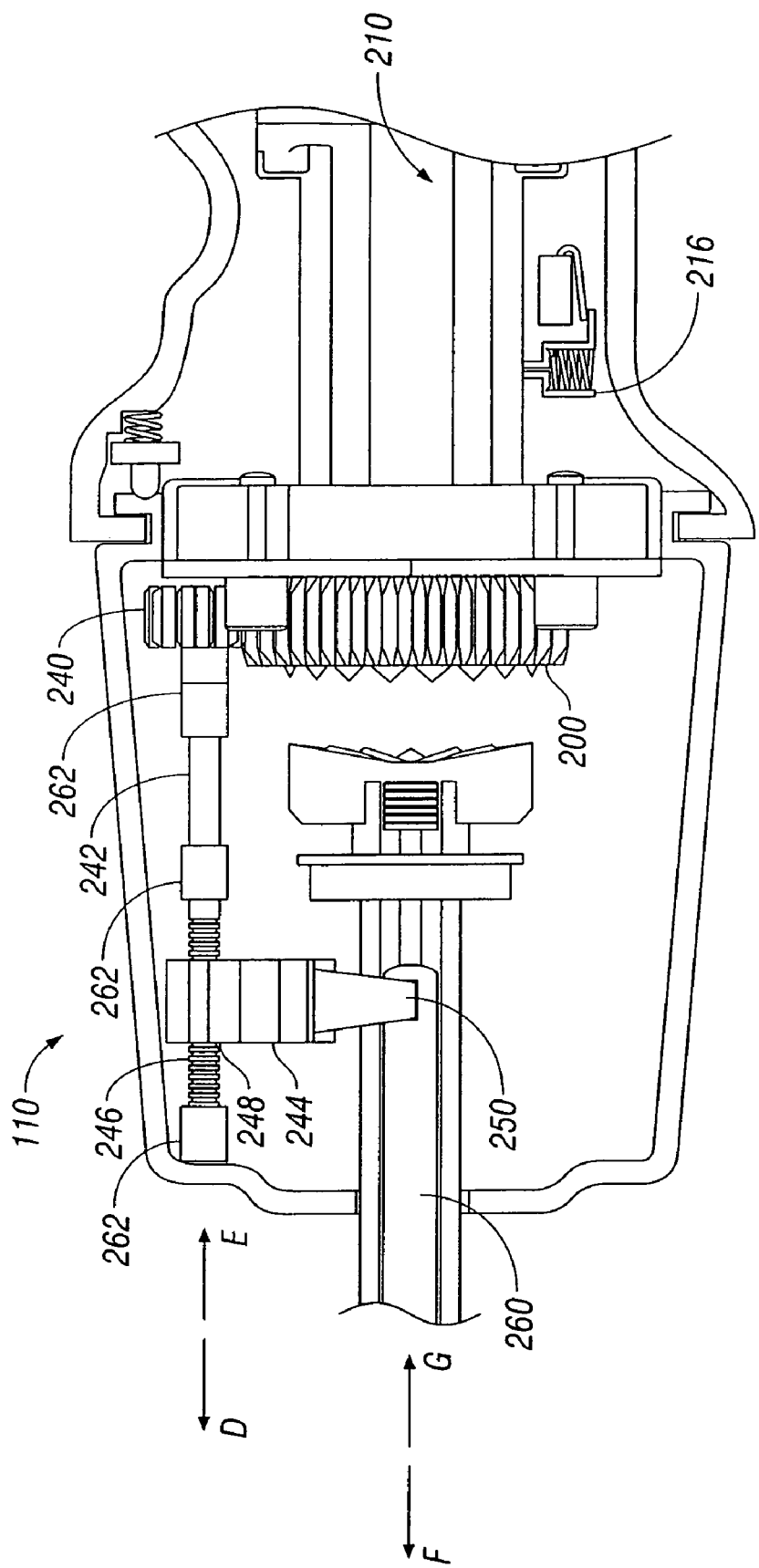
FIG. 7 is a cross-sectional view of the internal components of the powered surgical instrument of FIGS. 1-5 disposed in a second position.
Figure 9:
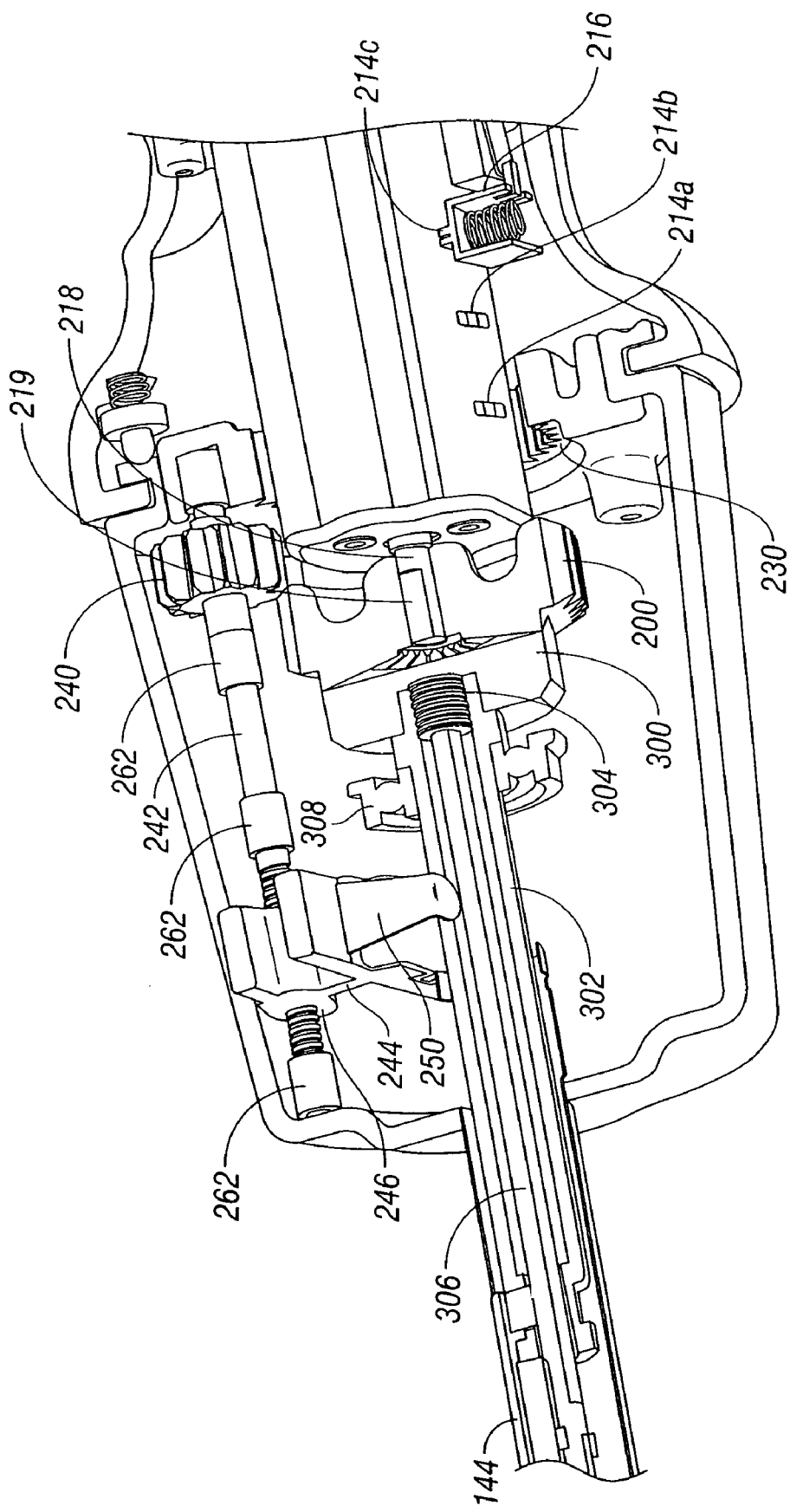
FIGS. 9-11 are partial perspective sectional views of the internal components of the powered surgical instrument of FIGS. 1-8 disposed in a third position.
Figure 10:
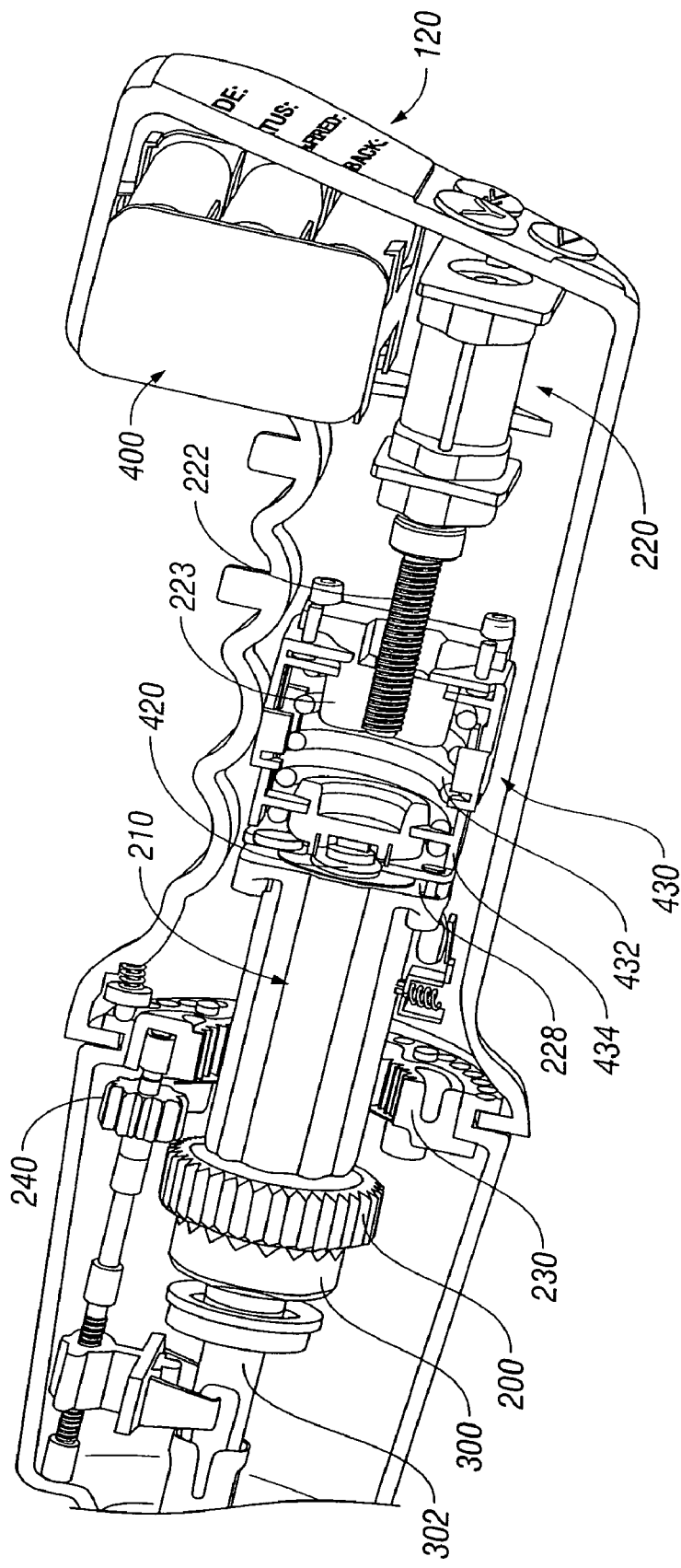
Figure 14:
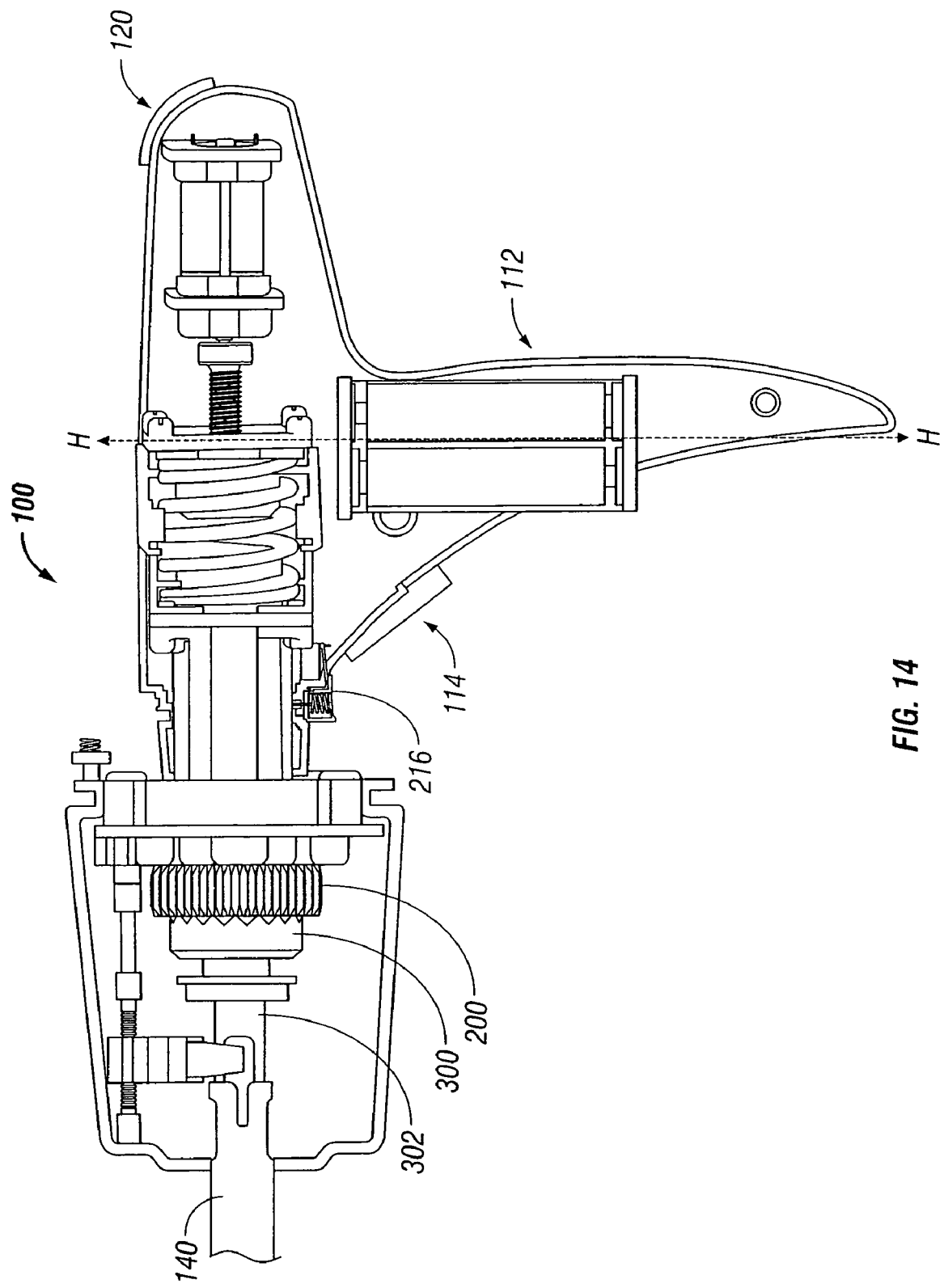
FIG. 14 is a cross-sectional view of a portion of a powered surgical instrument including a handle portion according to an embodiment of the present disclosure.

A cut-away view of drive motor casing 212, surrounding drive motor 210, is illustrated in FIGS. 4-7, 9-10 and 14. Drive motor casing 212 includes a plurality of slots 214 (three slots 214a, 214b and 214c are illustrated) therein. Each slot 214 is matable with a position lock 216 to maintain drive gear 210 in a desired position. For example, in FIG. 5, position lock 216 is shown mated with slot 214a—corresponding to drive gear 200 being in its first position. In FIG. 7, position lock 216 is shown mated with slot 214b—corresponding to drive gear 200 being in its second position. FIGS. 9, 10 and 14 illustrate position lock 216 mated with slot 214c—corresponding to drive gear 200 being in its third position. Position lock 216, in the illustrated embodiments, is spring-loaded towards drive motor casing 212, which helps place and maintain drive motor 210 is a desired position.

In the illustrated embodiments, shift motor 220 is located proximally of drive motor 210 and is configured to translate drive motor 210 along drive gear axis C-C between its first, second and third positions. Referring to FIG. 10, shift motor 220 is illustrated as driving a shift screw 222 in conjunction with an internally-threaded screw housing 223 (see FIG. 10), in accordance with a disclosed embodiment. It is further disclosed that a shift sensor 224 (see FIG. 4) (e.g., micro switch or optical/ferromagnetic proximity sensor activated by position lock 216), disposed adjacent position lock 216, electrically communicates with at least one switch 124 to start or stop shift motor 220 and/or provides feedback relating to the position of drive motor 210, for example the mode of operation for powered surgical instrument 100 is desirably displayed on screen 122. For instance, the position of drive motor 210 may be indicated on screen 122 of user interface 120.

With reference to FIGS. 5 and 6, the first position of drive gear 200 is illustrated. Here, a ring gear 230 or rotation member is disposed within housing 110 and rotation of ring gear 230 causes rotation of endoscopic portion 140, end effector 160 and a distal housing portion 110a of powered surgical instrument 100. It is envisioned that an inner surface of ring 230 includes threads and/or teeth to engage drive gear 200, and is attached to distal housing portion 110a, which is disposed distally of a proximal housing portion 110b. Further, distal housing portion 110a is rotatable with respect to proximal housing portion 110b via a peripherally disposed channel 232 disposed within distal housing portion 110a and a corresponding peripherally disposed flange 234 disposed within proximal housing portion 110b.

In an embodiment, ring gear 230 is rigidly secured within distal housing portion 110a and is matingly engagable with drive gear 200. Thus, rotation of drive gear 200 causes ring gear 230, and thus distal housing portion 110a to rotate. In FIG. 2, a lip 235 is shown which isolates a user's hand from rotatable distal housing portion 110a. It is envisioned that a plurality of washers or ball-bearings (possibly made from synthetic resinous fluorine-containing polymers sold under the trademark Teflon®) are disposed between distal housing portion 110a and proximal housing portion 110b to reduce the rotational friction therebetween.

With continued reference to the embodiment illustrated in FIG. 6, a plurality of detents 231 is disposed around a surface 233 of distal housing portion 110a. A tab 237 is shown disposed on proximal housing portion 110b and may comprise a pawl or spring-biased member. In a disclosed embodiment, tab 237 is distally biased and in mechanical cooperation with at least one of plurality of detents 231. The combination of detents 231 and tab 237 helps secure distal housing portion 110a in a rotational position with respect to proximal housing portion 110b. Further, detents 231 and tab 237 may be provided to give the user audible and/or tactile feedback when endoscopic portion 140 is rotated. In a disclosed embodiment, a three-position solenoid may be used to lock the rotational position of end effector 160 once the desired rotational position is selected.

In FIG. 7, drive gear 200 is illustrated in its second position, as position lock 216 is aligned with slot 214b. Here, drive gear 200 is matingly engaged with an articulation gear 240, which is disposed at least partially within housing 110. Rotation of articulation gear 240 causes end effector 160 to move from its first position, where longitudinal axis B-B is substantially aligned with longitudinal axis A-A, towards a position in which longitudinal axis B-B is disposed at an angle to longitudinal axis A-A. Preferably, a plurality of articulated positions are achieved.

In the illustrated embodiments and with specific reference to FIGS. 7 and 8, articulation of end effector 160 is affected by an articulation gear 240, an articulation screw 242, an articulation linkage 244 and at least one articulation rod 260. More specifically, articulation gear 240 is rigidly mounted to articulation screw 242, such that as articulation gear 240 is rotated by rotation of drive gear 200 while in its second position, articulation screw 242 also rotates. A plurality of bearings 262 is illustrated at various locations on articulation screw 242 to facilitate the retaining and aligning of articulation screw drive 242 as well as reducing the friction between articulation screw 242 and housing 110, for example.

With continued reference to FIG. 7, articulation screw 242 includes a threaded portion 246, which extends through an internally-threaded portion 248 of articulation linkage 244. This relationship between articulation screw 242 and articulation linkage 244 causes articulation linkage 244 to move distally and/or proximally (in the directions of arrows D and E) along threaded portion 246 of articulation screw 242 upon rotation of articulation screw 242. For example, as articulation screw 242 rotates in a first direction (e.g., clockwise), articulation linkage 244 move proximally, and as articulation screw 242 rotates in a second direction (e.g., counter-clockwise), articulation linkage 244 move distally.

At least one articulation arm 250 is shown extending from articulation linkage 244. In an embodiment, articulation arm 250 is rigidly connected to articulation rod 260 and it is envisioned that more than one articulation arm 250 is connectable to more than one articulation rod 260. As articulation linkage 244 is translated distally and/or proximally in response to rotation of articulation gear 240, articulation rod(s) 260 is also translated distally and/or proximally (in the directions of arrows F and G, along longitudinal axis A-A) in response thereto. Any combinations of limits switches, proximity sensors (e.g., optical and/or ferromagnetic), linear variable displacement transducers and shaft encoders (disposed within housing 110, for instance) may be utilized to control and/or record the location of articulation linkage 244 and/or articulation angle of end effector 160 and/or position of a firing rod 306 (as discussed below with reference to FIGS. 9 and 11).

Figure 8B:
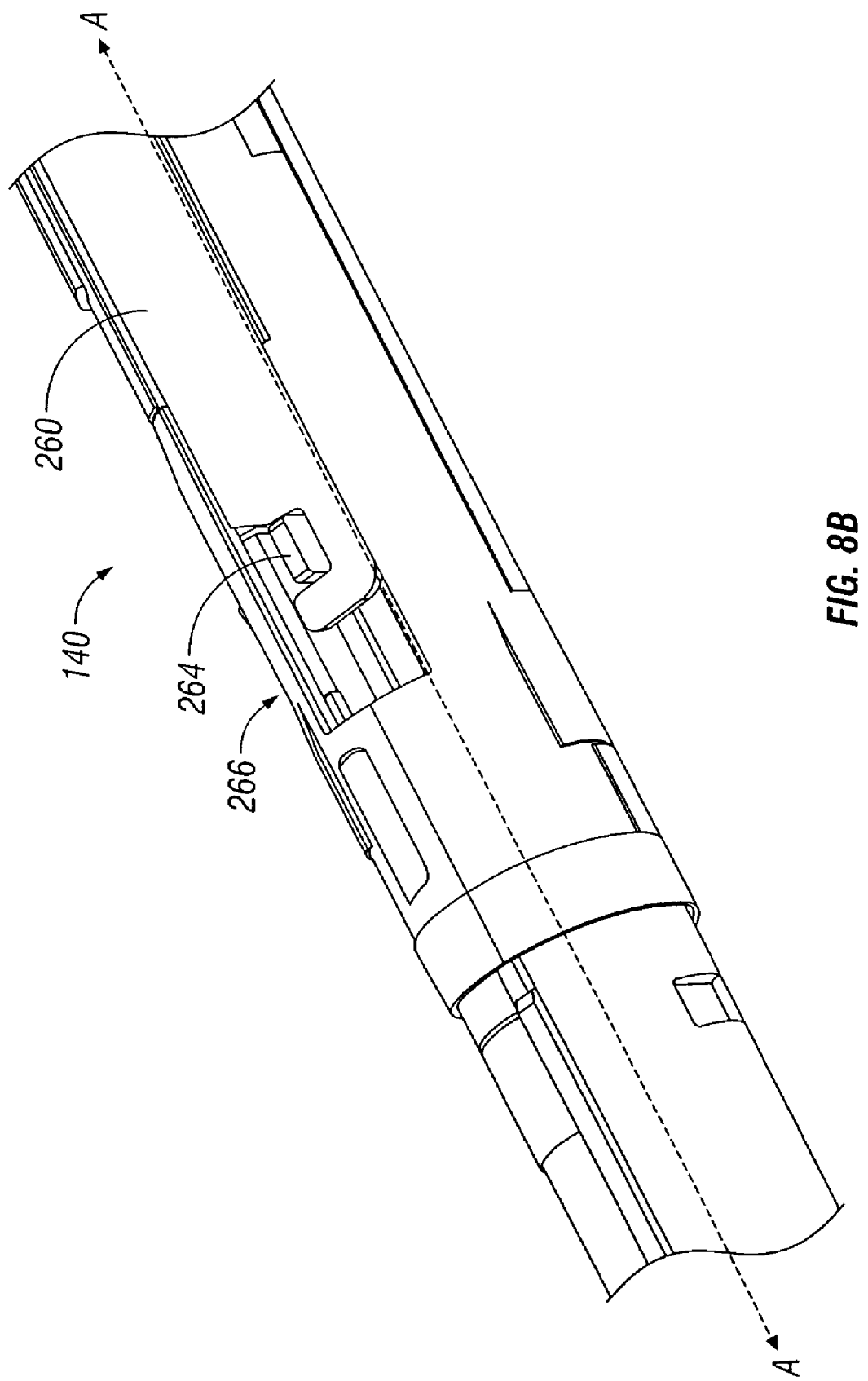
FIG. 8B is an enlarged perspective view of a portion of the powered surgical instrument indicated in FIG. 8A.

With reference to FIGS. 8A and 8B, articulation rod 260 is shown extending through at least a portion of endoscopic portion 140 and in mechanical cooperation with a linkage rod 264. Thus, linkage rod 264 similarly moves along longitudinal axis A-A upon rotation of articulation gear 240. A distal portion 266 of linkage rod 264 is in mechanical cooperation with end effector 160, such that proximal and distal movement of linkage rod 264 causes end effector 160 to move from its first position towards its second position about pivot P. For example, linkage rod 264 is connected to end effector 160 at a location offset laterally from pivot P. More specifically, and for illustrative purposes, as linkage rod 264 moves distally, end effector 160 is articulated in the direction of arrow H and as linkage rod 264 is translated proximally, end effector 160 is articulated in the direction of arrow I. It is also envisioned that a portion of articulation rod 260 is in mechanical cooperation with end effector 160 to affect articulation thereof. Further details of providing articulation to end effector 160 are described in detail in commonly-owned U.S. Pat. No. 6,953,139 to Milliman et al., the contents of which are hereby incorporated by reference in their entirety.

According to an embodiment of the present disclosure, end effector 160 includes a cartridge assembly (e.g., jaw member 164) and an anvil assembly (e.g., jaw member 162) including an anvil portion for deploying surgical fasteners into body tissue and forming the surgical fasteners. End effector 160 is pivotably mounted about an axis substantially perpendicular to the longitudinal axis of endoscopic portion 140. Cartridge assembly 164 houses a plurality of staples. Anvil assembly 162 is movable in relation to cartridge assembly 164 between an open position spaced from cartridge assembly 164 and an approximated or clamped position in juxtaposed alignment with cartridge assembly 164. Preferably, the staples are housed in cartridge assembly 164 to apply linear rows of staples to body tissue. End effector 160 is attached to a mounting portion, which is pivotably attached to a body portion. The body portion may be integral with endoscopic portion 140 of powered surgical instrument 100, or may be removably attached thereto to provide a replaceable or disposable loading unit. The loading unit may be connectable to endoscopic portion 140 through a bayonet connection. It is envisioned that the loading unit has an articulation link connected to the mounting portion of the loading unit and the articulation link is connected to the linkage rod so that the end effector 160 is articulated as the linkage rod is translated in the distal-proximal direction along the longitudinal axis. Other means of connecting end effector 160 to endoscopic portion 140 to allow articulation may be used. For example, a flexible tube or a plurality of pivotable members may be used.

Figure 15A:
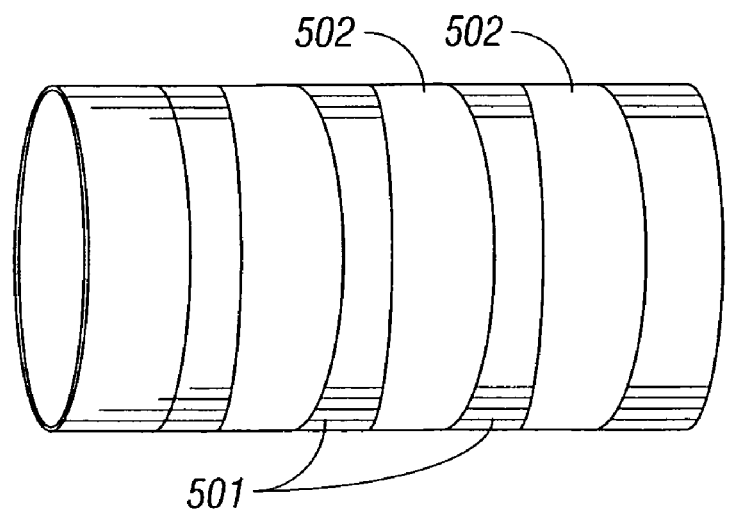
FIGS. 15A-B are perspective views of an articulating shaft of the distal portion of the powered surgical instrument of FIG. 1 according to an embodiment of the present disclosure.
Figure 15B:
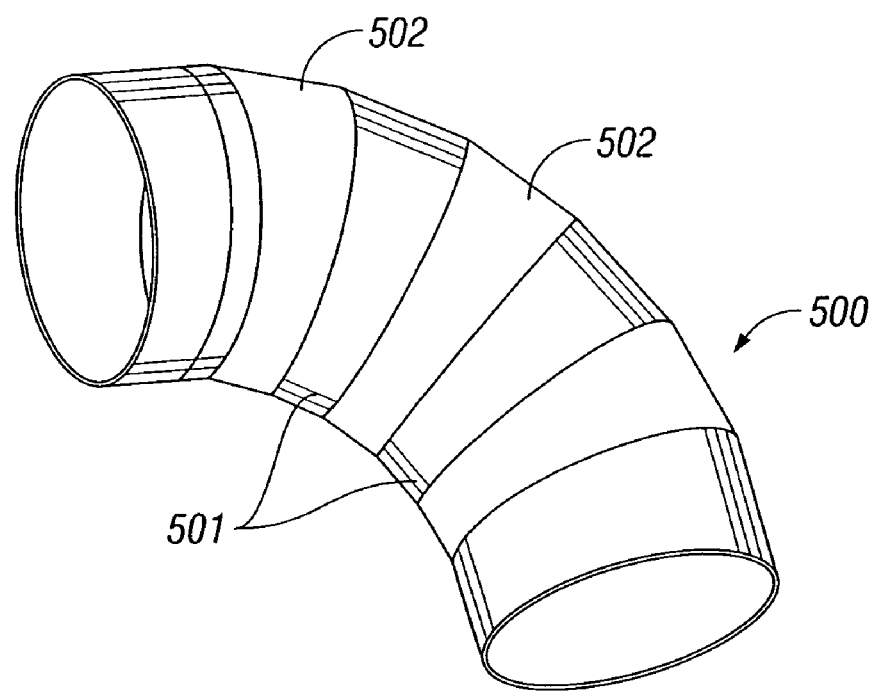

A loading unit may incorporate (or be configured to incorporate) various end effectors, such as vessel sealing devices, linear stapling devices, circular stapling devices, cutters, etc. Such end effectors may be coupled to endoscopic portion 140 of powered surgical instrument 100. An intermediate flexible shaft 500 may be included between handle portion 112 and loading unit. For example, as shown in FIGS. 15A-B, endoscopic and distal portions 140, 142 are shown as a flexible shaft 500. Flexible shaft 500 includes a plurality of interconnected angled outer tubes 501 and 502. FIG. 15A shows flexible shaft in a non-articulated formation and FIG. 15B shows flexible shaft 500 in an articulated formation. When flexible shaft 500 is straight, narrow sections of tubes 501 alternate with the wide sections of tubes 502 as shown in FIG. 15A. When flexible shaft 500 is fully articulated, the short sides and the wide sides of tubes 501 and 502 are aligned, as shown in FIG. 15B. Such a flexible shaft 500 may facilitate access in certain areas of the body. A system including more than one intermediate shaft may be used, each intermediate shaft being arranged to connect with one or more end effectors or loading units. Such intermediate shafts may include flexible, curved, rigid, telescoping, endoscopic, or other shafts.

Further, where various loading units can be used, a digital control module (DCM) 130 (FIG. 4) can control the force being applied to rod 306 so that rod 306 can drive the particular end effector that is on the loading unit in use at the time. For clarity, wires are not shown in the Figures connecting DCM 130 to various components of powered surgical instrument 100, but such wires are contemplated by the present disclosure. The loading unit may also include a mechanical or electronic sensor that indicates to DCM 130 which end effector is on the loading unit. In an embodiment, DCM 130 is also capable of storing information relating to the force applied to rod 306. Additionally, the voltage and current from drive motor 210 may be measured to provide information and/or feedback regarding the state of powered surgical instrument 100. For instance, if the user is attempting to clamp down on tissue that is too thick, the voltage and/or current will increase. This information can be provided to the user and/or the power can be interrupted or ceased. It is envisioned that such a feature helps prevent damage to the mechanisms in the instrument.

With reference to FIGS. 9-11 and 14, drive gear 200 is illustrated in its third position, with position lock 216 aligned with slot 214c. Here, drive gear 200 is matingly engaged with an actuator gear 300, which is disposed at least partially within housing 110. More specifically, a set of teeth 202 disposed on a face 204 (FIG. 4) of drive gear 200 matingly engage teeth on actuator gear 300 to provide at least one of grasping tissue, clamping tissue, and firing of end effector 160 (e.g., stapling and cutting) and retracting elements to their original position.

Figure 11:
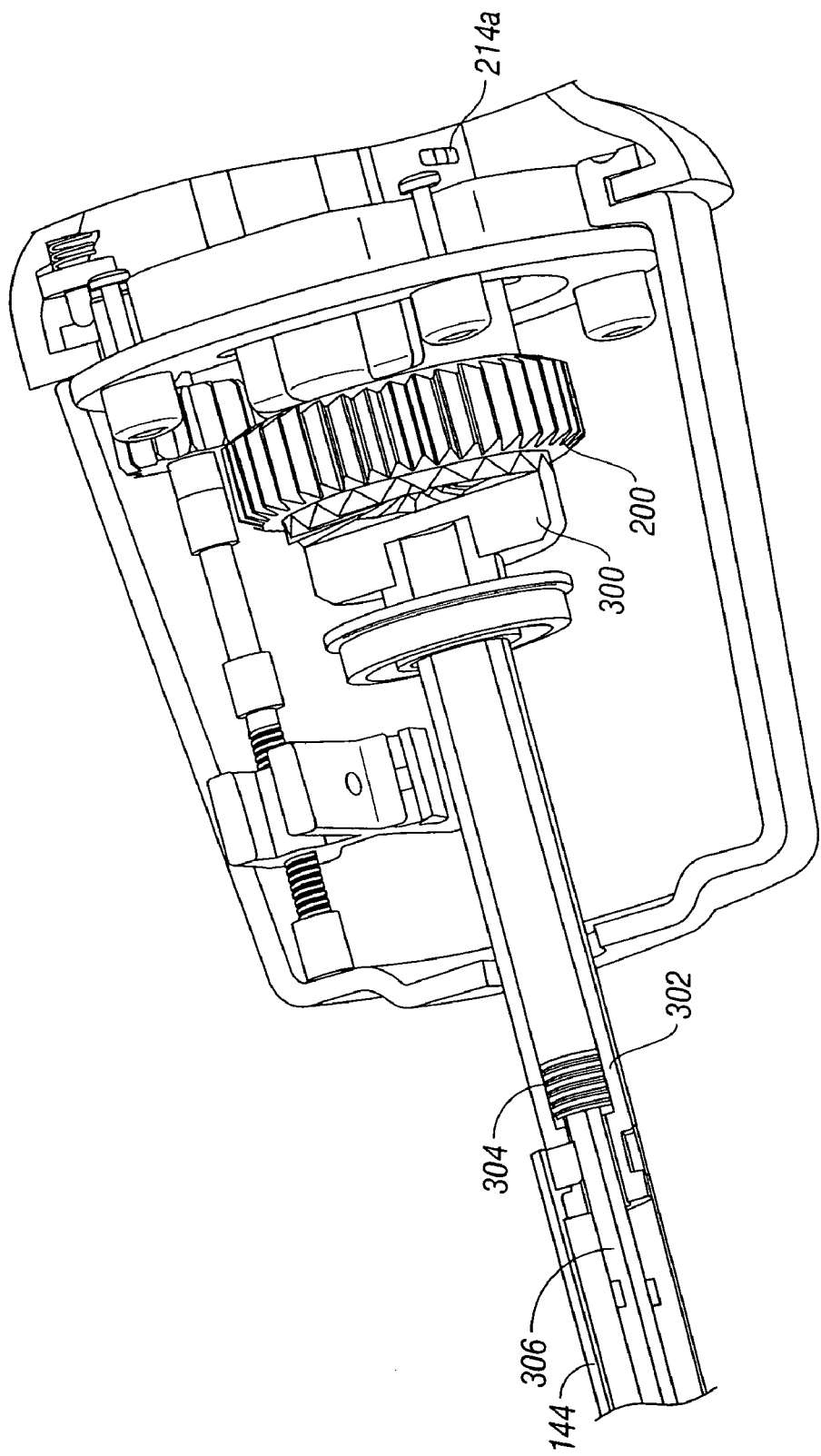

With continued reference to FIGS. 9 and 11, a drive tube 302, a bung 304 and firing rod 306 are also included. Drive tube 302 includes internal threads (not explicitly shown) along at least a portion of its length and is rigidly attached to actuator gear 300. Bung 304 is threadably engaged with internal threads of drive tube 302 and is translatable within drive tube 302 with respect to actuator gear 300. FIG. 9 shows bung 304 near its proximal-most position and FIG. 11 illustrates bung 304 near its distal-most position. Firing rod 306 is rigidly connected to bung 304 and extends distally therefrom. In an embodiment of the disclosure, firing rod 306 extends at least to distal portion 142 of endoscopic portion 140.

In response to rotation of drive gear 200, actuator gear 300 and drive tube 302 also rotate. As drive tube 302 rotates, bung 304 and firing rod 306 are translated proximally and/or distally within the confines of drive tube 302. Distal translation of firing rod 306 (corresponding with a clockwise rotation of drive gear 200, for instance) can cause jaw members 162, 164 (see FIG. 1) of end effector 160 to grasp or clamp tissue held therebetween. Additional distal translation of firing rod 306 may cause surgical fasteners to be ejected from end effector 160 (e.g., via cam bars and/or an actuation sled (neither of which are explicitly shown in this embodiment)) to fasten tissue and may also cause a knife (not explicitly shown in this embodiment) to sever tissue. Proximal translation of firing rod 306 (corresponding with a counter-clockwise rotation of drive gear 200, for instance) can cause jaw members 162, 164 and/or knife to return to their pre-fired positions. Further details of firing and otherwise actuating end effector 160 are described in detail in commonly-owned U.S. Pat. No. 6,953,139 to Milliman et al., the entire contents of which are hereby incorporated by reference herein.

In an embodiment of the disclosure, the anvil portion of end effector 160 includes a cam surface for being engaged by the drive assembly of end effector 160. The drive assembly includes a drive beam, which desirably has a knife for cutting tissue. The drive beam has a cam roller positioned to engage the cam surface, and a flange positioned to engage the cartridge assembly to effect approximation of the anvil assembly 162 and cartridge assembly 164 with respect to one another when the drive beam is advanced distally. In addition, when advanced further in the distal direction, the drive beam engages an actuation member for deploying the surgical fasteners from the cartridge assembly, as disclosed in the Milliman '139 patent.

Any combination of sensors may be positioned within powered surgical instrument 100 to determine the position of various components and/or its operating stage, e.g., articulation, rotation, clamping, firing of end effector 160. For example, limit switches, proximity sensors (e.g., linear and/or ferromagnetic), potentiometers, linear variable displacement transducers (LVDT), shaft encoders, etc., may be used to help control and/or record the location of articulation linkage 244, firing rod 306 and/or ring gear 230, as discussed above.

Figure 12:
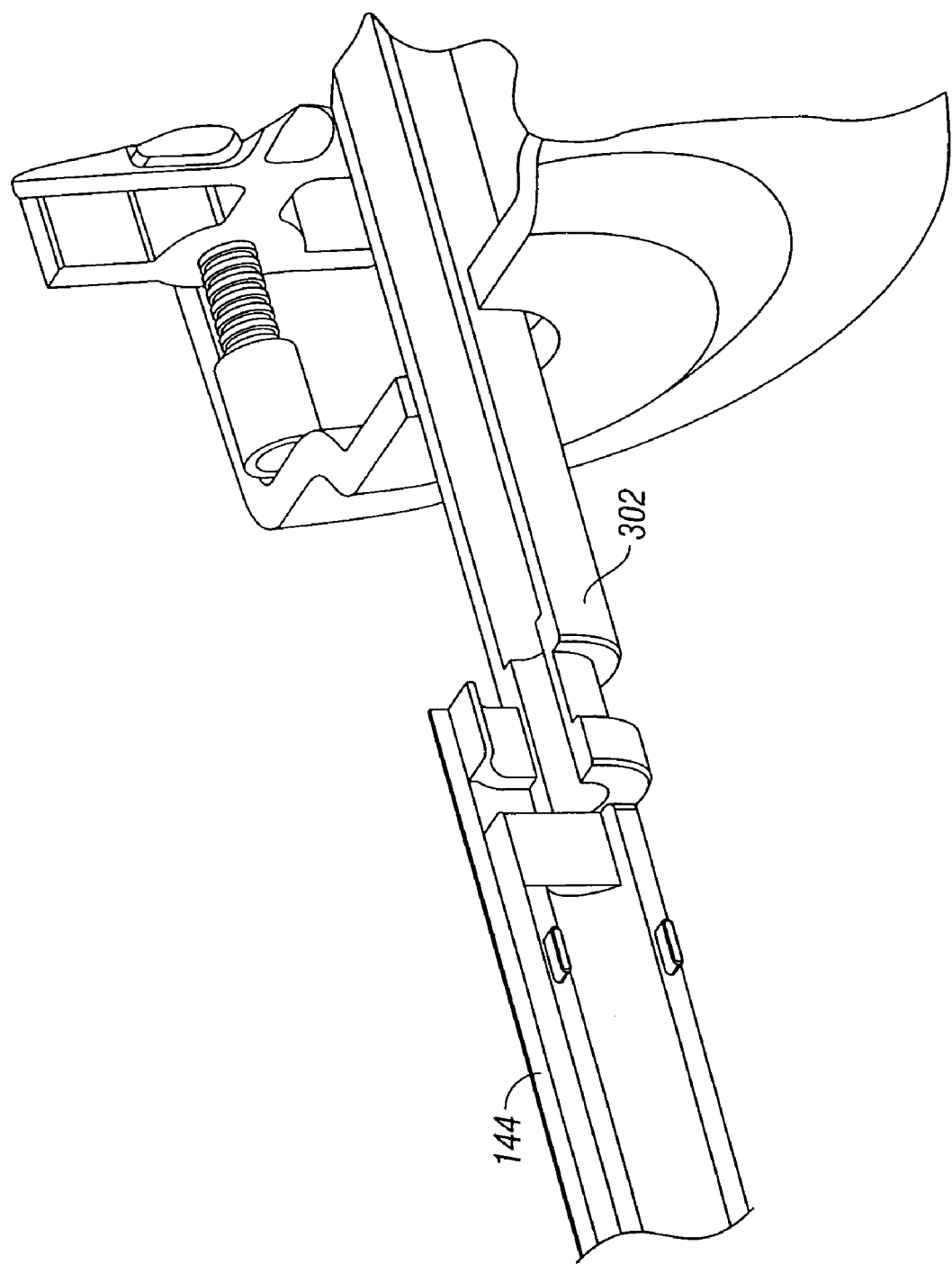
FIGS. 12 and 13 are enlarged perspective views of portions of the powered surgical instrument of FIGS. 1-11 according to an embodiment of the present disclosure.
Figure 13:
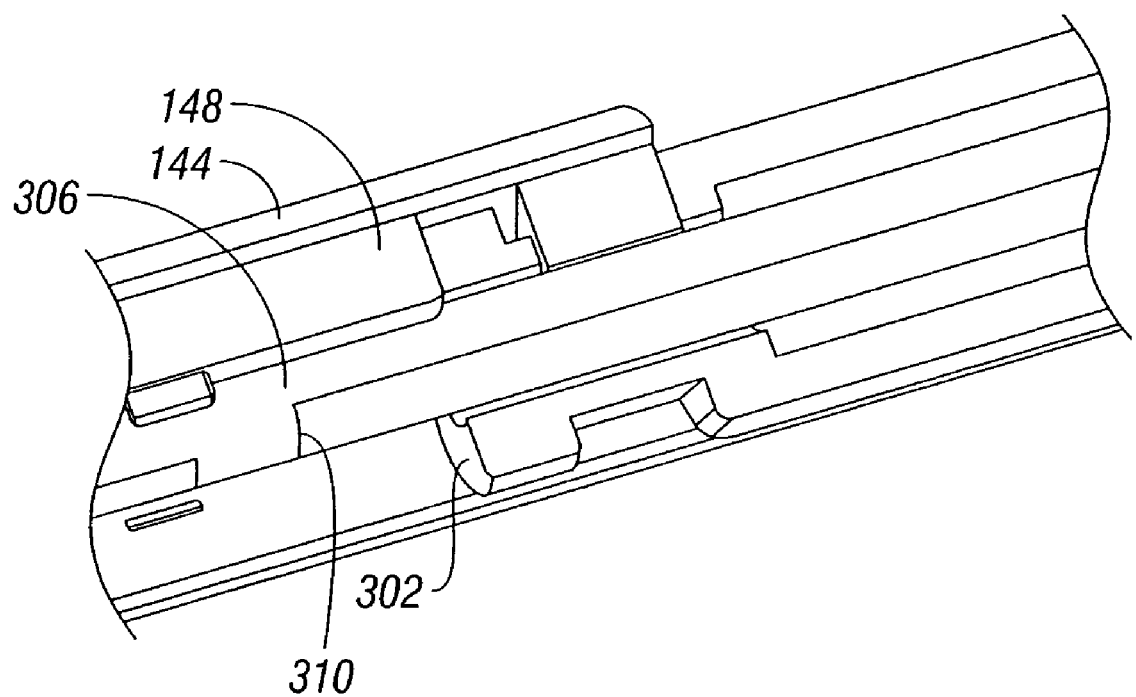

Referring now to FIGS. 9, 11 and 12, endoscopic portion 140 includes a tube housing 144 that extends from an area adjacent housing 110 towards end effector 160. As drive tube 302 rotates, end effector 160 does not rotate as a direct consequence thereof. Referring to FIG. 13, tube housing 144 includes flat portions 148 thereon, which correspond to flat portions 310 of firing rod 306. The pair of flat portions 148 and 310 helps prevent rotation of firing rod 306 by helping to limit firing rod 306 to axial movement.

With reference to FIG. 9, a drive motor shaft 218 is shown extending from drive motor 210 and being connected to drive gear 200. A fastener (not explicitly shown in this embodiment) may be used to retain drive gear 220 on drive motor shaft 218. Drive motor shaft 218 is rotated by drive motor 210, thus resulting in rotation of drive gear 220. Drive motor shaft 218 is shown having a flat portion 219 (more than one flat portions 219 may be included), which allows "play" or "rotational float" between drive gear 220 and drive motor shaft 218 to facilitate tooth alignment of the gears and to help enable drive gear 220 to shift between positions. FIG. 9 also illustrates a bearing 308 disposed within housing 110 and at least partially surrounding drive tube 302. Bearing 308 facilitates rotation of drive tube 302 and helps to align drive tube 302 through endoscopic portion 140 and supports all thrust loading between drive gear 200 and actuator gear 300.

In FIG. 10, a transducer 420 is shown adjacent drive motor 210 and shift motor 220. Transducer 420 (e.g., a force or pressure transducer) may measure and/or control the force required for the desired pressure on actuator gear 300. Transducer 420 may be in communication with portions of user interface 120, which may provide feedback to a user. Additionally, spring coupling 430 is illustrated between drive motor 210 and shift motor 220. Specifically, in a disclosed embodiment, spring coupling 430 includes a spring 432 mounted in a telescoping cage 434. Shift screw 222 is shown extending through spring 432 and may be configured to apply a compressive load on spring 432. It is envisioned that cage 434 is collapsible as spring 432 is compressed. The force applied to drive motor 210 may be adjusted using spring 432 and/or cage 434.

In an embodiment of the disclosure, drive gear 200 and actuator gear 300 form a clutch face. The gear teeth are arranged to slip unless a threshold force is applied to drive motor 210 by shift motor 200 and a spring coupling 430 (as discussed below in connection with FIG. 10) disposed therebetween. Further, when shift motor 200 and spring coupling 430 apply the threshold force needed for drive gear 200 and actuator gear 300 to engage without slipping, rod 306 will be driven distally. Telescoping cage 434 may include a stop incorporated therewith, such that cage 434 will retract rod 306, rather than decompress spring coupling 430.

With reference to FIG. 3, user interface 120 is shown including screen 122 and seven switches 124a-124g. In the illustrated embodiment, user interface displays the "mode" (e.g., rotation, articulation or actuation), which may be communicated to user interface 120 via shift sensor 224 (FIG. 4), "status" (e.g., angle of articulation, speed of rotation, or type of actuation) and "feedback," such as whether staples have been fired. Switch 124a is shown having an "M," standing for mode, which may be used to position drive gear 200 via shift motor 220 for selecting between rotation, articulation, grasping, clamping and firing. It is also envisioned that switch 124a can be used to let a user input different tissue types, and various sizes and lengths of staple cartridges.

Switches 124b-124e on user interface 120 are shown with arrows thereon and may be used for selecting the direction, speed and/or torque at which drive gear 200 is rotated by drive motor 210. It is also envisioned that at least one switch 124 can be used for selecting an emergency mode that overrides various settings, for example. Further, switches 124f and 124g are illustrated having an "N" and a "Y" thereon. It is envisioned that switches 124f and 124g may be used for helping a user navigate and select various setting of powered surgical instrument 100. The indicia on switches 124a-124g and their respective functions are not limited by what is shown in the accompanying figures, as deviations therefrom are contemplated and within the scope of the present disclosure. Additionally, and with reference to FIGS. 1 and 2, buttons 114a and 114b may be used for starting and/or stopping movement of drive motor 210 and/or shift motor 220. Other functions for buttons 114 and 114b are also anticipated as well as having more or fewer buttons 114. In a particular embodiment, switches 124a-124g may include one or more microelectronic membrane switches, for example. Such a microelectronic membrane switch includes a relatively low actuation force, small package size, ergonomic size and shape, low profile, the ability to include molded letters on the switch, symbols, depictions and/or indications, and a low material cost. Further, switches 124a-124g (such as microelectronic membrane switches) may be sealed to help facilitate sterilization of powered surgical instrument 100, as well as helping to prevent particle and/or fluid contamination.

As an alternative to, or in addition to switches 124 or buttons 114, other input devices may include voice input technology, which may include hardware and/or software incorporated in a digital control module (DCM) 130 (FIG. 4), or a separate digital module connected to DCM 130. The voice input technology may include voice recognition, voice activation, voice rectification and/or embedded speech. The user may be able to control the operation of the instrument in whole or in part through voice commands, thus freeing one or both of the user's hands for operating other instruments. Voice or other audible output may also be used to provide the user with feedback.

In an embodiment, spring coupling 430 is used in the feedback and control of powered surgical instrument 100. As described above, DCM 130 may be connected to one or more buttons 114 or switches 124 and one or more display screens 122 to provide feedback to the user and for helping to control the operation of powered surgical instrument 100. DCM 130 may be a digital board incorporated in housing 110 of powered surgical instrument 100. Spring coupling 430 may include a pressure transducer that can interact with DCM 130 to control the force being applied to rod 306.

It is also envisioned that user interface 120 includes different colors and/or intensities of text on screen 122 and/or on switches 124a-124g for further differentiation between the displayed items. User feedback can also be included in the form of pulsed patterns of light, acoustic feedback (e.g., buzzers, bells or beeps that may be sounded at selected time intervals), verbal feedback, and/or haptic vibratory feedback (such as an asynchronous motor or solenoids), for example. The visual, auditory or haptic feedback can be increased or decreased in intensity. For example, the intensity of the feedback may be used to indicate that the forces on the instrument are becoming excessive. Additionally, switches 124a-124g may be positioned at different heights from one another and/or may included raised indicia or other textural features (e.g., concavity or convexity) to allow a user to depress an appropriate switch 124 without the need to look at user interface 120. Further, proximal housing portion 110b may be used as a joy stick-type control system.

Additionally, user interface 120 may include a separate display screen or screens 122 and input devices (such as switches 124 or buttons 114), or the input devices may be incorporated in whole or in part in screen 122. For example, a touch screen liquid crystal display (LCD) may be used to allow the user to provide input while viewing operational feedback. The touch screen LCD may include resistive, capacitive or surface acoustic wave controls. This approach may enable facilitation of sealing screen 122 components to help sterilize powered surgical instrument 100, as well as preventing particle and/or fluid contamination. In certain embodiments, screen 122 is pivotably or rotatably mounted to powered surgical instrument 100 for flexibility in viewing screen 122 during use or preparation. Screen 122 may be hinged or ball-and-socket mounted to powered surgical instrument 100, for example.

In a disclosed embodiment, at least some of the information monitored by the various sensors in powered surgical instrument 100 may be provided to a video screen or monitoring system in an operating room. For instance, the data may be transmitted to a receiver for the operating room monitoring system from a communication transmitter incorporated in or associated with powered surgical instrument 100, via technology including Blue Tooth, ANT3, KNX, Z Wave, X10, wireless USB, WiFi, IrDa, Nanonet, Tiny OS, ZigBee, radio, UHF and VHF. Such features may facilitate monitoring by the user of powered surgical instrument 100 or other operating room or hospital personnel or remotely located persons.

Figure 4:
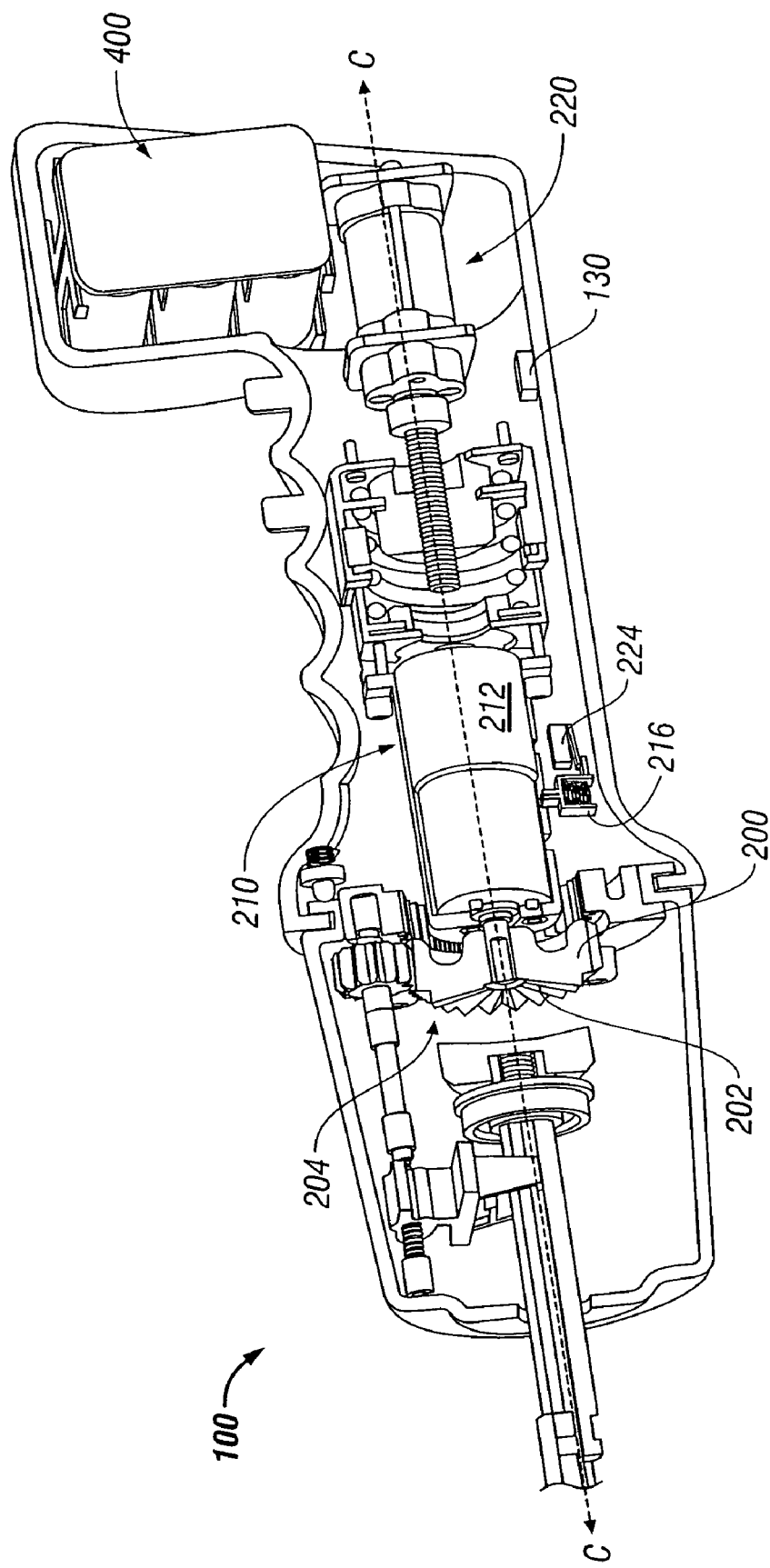
FIG. 4 is a partial perspective sectional view of internal components of the powered surgical instrument of FIGS. 1-3 in accordance with an embodiment of the present disclosure.

Referring to FIG. 4, any combination of a battery pack 400, fuel cell and/or high-energy capacitor may be used to provide power to powered surgical instrument 100. For example, capacitors may be used in conjunction with battery pack 400. Here, capacitors can be used for a burst of power when energy is desired/required more quickly than can be provided with a slow-drain battery on its own (e.g., when clamping thick tissue, rapid firing, clamping, etc.), from which current cannot be quickly drawn. It is envisioned that batteries can be connected to capacitors to charge the capacitors.

It is also envisioned that battery pack 400 includes at least one disposable battery. The disposable battery or batteries may be between about 9 volts and about 30 volts and may be useful in a disposable surgical instrument which is ready to use without requiring hospital staff to connect the instrument to a generator or to charge batteries. The higher voltage batteries are desirable because they draw less current in normal use, they are efficient, and can handle spikes in power. Other power-supplying means are also contemplated including electric power. In alternative embodiments a cord is provided to connect instrument 100 to a generator.

In a disclosed embodiment, the DCM is connected to shift motor 220 and drive motor 210 and is configured and arranged to monitor the battery 400 impedance, voltage, temperature and/or current draw and to control the operation of powered surgical instrument 100. The load or loads on battery 400, transmission, motors 220, 210 and drive components of powered surgical instrument 100 are determined to control a motor speed if the load or loads indicate a damaging limitation is reached or approached. For example, the energy remaining in battery 400, the number of firings remaining, whether battery 400 must be replaced or charged, and/or approaching the potential loading limits of powered surgical instrument 100 may be determined.

The DCM can be configured and arranged to control or help control the operation of shift motor 220 and/or drive motor 210 to respond to the monitored information. Pulse modulation, which may include an electronic clutch, may be used in controlling the output. For example, the DCM can regulate the voltage or pulse modulate the voltage to adjust the power and/or torque output to prevent system damage or optimize energy usage. An electric braking circuit may be used for controlling the drive motor 210 and/or shift motor 220, which uses the existing back electromotive force (EMF) of rotating drive motor 210 to counteract and substantially reduce the momentum of drive gear 200. The electric braking circuit may improve the control of drive motor 210 and/or shift motor 220 for stopping accuracy and/or shift location of powered surgical instrument 100. Sensors for monitoring components of powered surgical instrument 100 and to help prevent overloading of powered surgical instrument 100 may include thermal-type sensors, such as thermal sensors, thermistors, thermopiles, thermo-couples and/or thermal infrared imaging and provide feedback to the DCM. The DCM may control the components of powered surgical instrument 100 in the event that limits are reached or approached and such control can include cutting off the power from the battery pack 400, temporarily interrupting the power or going into a pause mode, pulse modulation to limit the energy used, and the DCM can monitor the temperature of components to determine when operation can be resumed. The above uses of the DCM may be used independently of or factored with current, voltage, temperature and/or impedance measurements.

In the embodiment illustrated in FIG. 5, shift motor 220 is shown including a two-part housing 226. Each part 226a and 226b of two-part housing 226 are slidably engaged with each other. It is envisioned that part 226a is rigidly secured to drive motor casing 212, while part 226b is affixed to shift motor 220 and is translatable within housing 110. Additionally, a wiring slot 228 may be included to allow for wires (not explicitly shown in this embodiment) to pass from transducer 420 towards user interface 120, for example (see also FIG. 10).

Referring to FIG. 14, powered surgical instrument 100 is illustrated having a pistol-grip handle portion 112. Here, handle portion 112 is disposed at an angle (e.g., substantially 90°) from longitudinal axis A-A. In this embodiment, it is envisioned that at least one button 114 is disposed thereon. Additionally, user interface 120 may be positioned approximately in the position shown in FIG. 14. Further, a movable handle (not explicitly shown in this embodiment) may be employed to control various functions of powered surgical instrument 100.

It is envisioned that end effector 160 is reusable, can accept a staple cartridge and/or is part of a disposable loading unit. Further details of a disposable loading unit are described in detail in commonly-owned U.S. Pat. No. 5,752,644 to Bolanos et al., the entire contents of which are hereby incorporated by reference herein. Disposable and/or replaceable loading units can include end effectors without articulation, as disclosed in U.S. Pat. No. 6,953,139 to Milliman et al., previously incorporated by reference. A switch may be provided adjacent handle portion 112 to deactivate the second position of shift motor 220 electronically. Other means, such as mechanical means, may also be used.

A disposable or replaceable loading unit incorporating a surgical end effector 160, in certain embodiments of the present disclosure, includes sensors positioned within the loading unit to determine the position of various components and/or operation of end effector 160, such as articulation, rotation, clamping and firing of end effector 160. For example, electrical contacts, proximity sensors, optical sensors, photo diodes, and/or mechanical or metallic sensors are used to control and/or record information concerning the end effector 160. The location of the anvil assembly 162 and cartridge assembly 164 with respect to one another, the articulated or non-articulated position of end effector 160, rotation of end effector 160, and/or correct loading of the loading unit, staple cartridge and/or components of the staple cartridge may also be determined.

An identification system may also be included to determine and communicate to the DCM various information, including the speed, power, torque, clamping, travel length and strength limitations for operating the particular end effector 160. The DCM may also determine the operational mode and adjust the voltage, clutch spring loading and stop points for travel of the components. More specifically, the identification system may include a component (e.g., a microchip, emitter or transmitter) in end effector 160 that communicates (e.g., wirelessly, via infrared signals, etc.) with the DCM, or a receiver therein. It is also envisioned that a signal may be sent via firing rod 306, such that firing rod 306 functions as a conduit for communications between the DCM and end effector 160. The identification system communicates with the DCM information concerning the surgical instrument, such as, for example, the type of end effector attached to the surgical instrument and/or the status of the end effector.

The loading unit, in certain embodiments according to the present disclosure, includes an axial drive assembly that cooperates with firing rod 306 to approximate anvil assembly 162 and cartridge assembly 164 of end effector 160, and fire staples from the staple cartridge. The axial drive assembly may include a beam that travels distally through the staple cartridge and may be retracted after the staples have been fired, as disclosed in certain embodiments of U.S. Pat. No. 6,953,139 to Milliman et al., the disclosure of which is hereby incorporated by reference herein. By way of example, the sensors discussed above may be used to determine if the staples have been fired from the staple cartridge, whether they have been fully fired, whether and the extent to which the beam has been retracted proximally through the staple cartridge and other information regarding the operation of the loading unit. In certain embodiments of the present disclosure, the loading unit incorporates components for identifying the type of loading unit, and/or staple cartridge loaded on the instrument 100, including infra red, cellular, or radio frequency identification chips (such as Sensormatic or similar technology). The type of loading unit and/or staple cartridge may be received by an associated receiver within the DCM, or an external device in the operating room for providing feedback, control and/or inventory analysis. The power or battery pack 400 can incorporate a component for identifying the type of power pack 400 loaded with powered surgical instrument 100 or for sending feedback concerning the status of power pack 400.

In certain embodiments of the present disclosure, powered surgical instrument 100 includes disposable or replaceable loading units incorporating a surgical end effector 160 and a reusable portion including a housing 110 and endoscopic portion 140 that is removably attached to the loading unit. The reusable portion may be configured for sterilization and reuse in a subsequent surgical procedure. In an embodiment, the components of the housing 110 are sealed against infiltration of particulate and/or fluid contamination and help prevent damage of the component by the sterilization process. Power pack 400, in certain embodiments according to the present disclosure, comprises a rechargeable battery. The rechargeable battery can be connected to contacts accessible at housing 110 of the instrument 100, for example, or, rechargeable battery may be rechargeable through an inductive charging interface sealed within housing 110. The inductive charging interface may eliminate shorting of contacts and provides an internal battery that may be hermetically or liquid resistance sealed.

The present disclosure also relates to a method of applying surgical fasteners to tissue. The method includes the use of powered surgical instrument 100, as described above.

It will be understood that various modifications may be made to the embodiments disclosed herein. For example, a shorter elongated tubular portion containing more or less coil fasteners may be provided for greater ease of handling during open surgery. Various articulations may be provided along the length of the elongated tubular portion to facilitate positioning of the coil fastener applier within the body. Additionally various configurations of the drive rod and slots or fastener retaining structure may be provided to accommodate various types of rotary fasteners. The locations along the longitudinal axis for drive motor 210 and/or drive gear 200 may be different than shown. Different types of gears for driving, rotation, articulation and/or actuation may be used. Therefore, the above description should not be construed as limiting, but merely as exemplifications of various embodiments. Those skilled in the art will envision other modifications within the scope and spirit of the claims appended hereto.

The invention claimed is:

1. A surgical instrument, comprising:
   a housing;
   an endoscopic portion extending distally from the housing and defining a longitudinal axis;
   a drive gear disposed at least partially within the housing, the drive gear rotatable about a drive gear axis extending therethrough and being selectively movable along the drive gear axis;
   a drive motor including a drive motor shaft extending distally therefrom, the drive motor shaft being mechanically engaged with the drive gear and being configured to rotate the drive gear;
   a shift motor disposed in mechanical cooperation with the drive gear and being configured to move the drive gear along the drive gear axis;
   an end effector disposed in mechanical cooperation with the drive gear and being adjacent a distal portion of the endoscopic portion; and
   a shift sensor associated with the shift motor and arranged to determine the position of the drive gear;
   wherein the shift motor is configured to move the drive motor along the drive gear axis, and wherein the shift sensor is arranged to determine the longitudinal position of the drive motor.

2. The surgical instrument according to claim 1, wherein the housing includes a screen for displaying information concerning the status of the surgical instrument.

3. The surgical instrument according to claim 1, further comprising at least one switch for controlling the surgical instrument.

4. The surgical instrument according to claim 1, further comprising a shift screw, the shift motor driving the shift screw.

5. The surgical instrument according to claim 4, further comprising a screw housing, the shift screw being in engagement with the screw housing for moving the screw housing longitudinally.

6. The surgical instrument according to claim 1, wherein information from the shift sensor is communicated to a screen associated with the instrument.

7. The surgical instrument according to claim 6, wherein the screen is a touch screen.

8. The surgical instrument according to claim 1, wherein the shift sensor communicates with at least one switch to start or stop the shift motor.

9. The surgical instrument according to claim 1, further comprising a position lock for engaging the drive motor in one of a plurality of positions.

10. The surgical instrument according to claim 9, wherein the shift sensor interacts with the position lock to determine the status of the shift motor.

11. The surgical instrument according to claim 10, wherein the status of the shift motor is communicated to a screen associated with the instrument.

12. The surgical instrument according to claim 1, wherein the drive gear axis and the longitudinal axis are coaxial.

13. The surgical instrument according to claim 1, wherein the drive motor shaft includes a longitudinally flat portion which is configured to allow rotational float between the drive motor shaft and the drive gear.

14. The surgical instrument according to claim 1, wherein the drive gear is selectively movable along the drive gear axis between a proximal-most position and a distal-most position, and wherein the drive motor is disposed proximally of the proximal-most position of the drive gear.

15. The surgical instrument according to claim 1, wherein the drive motor shaft is connected to the drive gear.

16. A surgical instrument, comprising:
a housing;
an endoscopic portion extending distally from the housing and defining a longitudinal axis;
a drive gear disposed at least partially within the housing, the drive gear rotatable about a drive gear axis extending therethrough and being selectively movable along the drive gear axis;
a drive motor including a drive motor shaft extending distally therefrom, the drive motor shaft being mechanically engaged with the drive gear and being configured to rotate the drive gear;
a shift motor disposed in mechanical cooperation with the drive gear and being configured to move the drive gear along the drive gear axis;
an end effector disposed in mechanical cooperation with the drive gear and being adjacent a distal portion of the endoscopic portion;
a shift sensor associated with the shift motor and arranged to determine the position of the drive gear;
a position lock for engaging the drive motor in one of a plurality of positions, wherein the position lock is configured for engaging the drive motor in one of a plurality of longitudinally spaced positions; and
a drive motor casing at least partially surrounding the drive motor, the drive motor casing including at least three slots therein, wherein each slot is matable with the position lock to maintain the drive gear in a desired longitudinal position.

17. The surgical instrument according to claim 16, wherein the housing includes a screen for displaying information concerning the status of the surgical instrument.

18. The surgical instrument according to claim 16, further comprising at least one switch for controlling the surgical instrument.

19. The surgical instrument according to claim 16, further comprising a shift screw, the shift motor driving the shift screw.

20. The surgical instrument according to claim 19, further comprising a screw housing, the shift screw being in engagement with the screw housing for moving the screw housing longitudinally.

21. The surgical instrument according to claim 16, wherein information from the shift sensor is communicated to a screen associated with the instrument.

22. The surgical instrument according to claim 21, wherein the screen is a touch screen.

23. The surgical instrument according to claim 16, wherein the shift sensor communicates with at least one switch to start or stop the shift motor.

24. The surgical instrument according to claim 16, wherein the shift sensor interacts with the position lock to determine the status of the shift motor.

25. The surgical instrument according to claim 24, wherein the status of the shift motor is communicated to a screen associated with the instrument.

26. The surgical instrument according to claim 16, wherein the drive gear axis and the longitudinal axis are coaxial.

27. The surgical instrument according to claim 16, wherein the drive motor shaft includes a longitudinally flat portion which is configured to allow rotational float between the drive motor shaft and the drive gear.

28. The surgical instrument according to claim 16, wherein the drive gear is selectively movable along the drive gear axis between a proximal-most position and a distal-most position, and wherein the drive motor is disposed proximally of the proximal-most position of the drive gear.

* * * * *